United States Patent [19]

Schroepfer, Jr. et al.

[11] 4,202,891

[45] May 13, 1980

[54] 15-OXYGENATED STEROL COMPOUNDS AND THE USE OF SUCH COMPOUNDS TO INHIBIT THE BIOSYNTHESIS OF STEROLS

[76] Inventors: George J. Schroepfer, Jr.; Edward J. Parish, both of P.O. Box 1892, Houston, Tex. 77001; Andrew A. Kandutsch, 31 Eagle Lake Rd., Bar Harbor, Me. 04609

[21] Appl. No.: 797,345

[22] Filed: May 16, 1977

[51] Int. Cl.² .......................... A61K 31/56; C07J 9/00
[52] U.S. Cl. .................................. 424/242; 424/238; 424/243; 260/397.2
[58] Field of Search ..................... 260/397.2; 424/238, 424/243, 242

[56] References Cited

U.S. PATENT DOCUMENTS

| 3,287,380 | 11/1966 | Miki et al. | 260/397.45 |
|---|---|---|---|
| 3,354,154 | 11/1967 | Edwards et al. | 260/397.5 |

OTHER PUBLICATIONS

Martin et al., "Biochemical and Biophysical Research Communications," vol. 39, No. 6 (1970).
Knight et al., "The Journal of Biological Chemistry," Apr. 10, 1966.

*Primary Examiner*—Alan L. Rotman
*Assistant Examiner*—Robert C. Whittenbaugh
*Attorney, Agent, or Firm*—Finnegan, Henderson, Farabow, Garrett & Dunner

[57] ABSTRACT

15-oxygenated sterols, having the ability to inhibit the biosynthesis of mevalonic acid, and produce other effects derived from their ability to inhibit the biosynthesis of mevalonic acid, are disclosed. The 15-oxygenated sterols correspond to the structural formula:

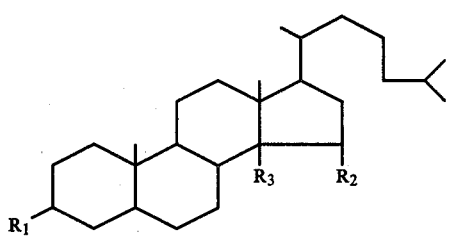

where:
$R_1$ is —OH, =O, —OR$_4$,

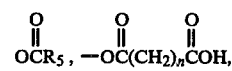

a sulfate group, or a Mg, Na, or K salt of a sulfate group;
$R_2$ is —OH, =O, or

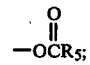

$R_3$ is $\alpha$H, $\beta$H, or an $\alpha$C$_1$ to C$_6$ alkyl group;
$R_r$ is a C$_1$ to C$_6$ alkyl group and preferably a C$_1$ to C$_3$ alkyl group;
$R_5$ is a C$_1$ to C$_{20}$ aliphatic group, a substituted C$_1$ to C$_{20}$ aliphatic group, or a phenyl group; and
n is a whole number from 2 to 6 and preferably from 2 to 4.

The basic ring structure may be saturated or unsaturated, and when it is possible for the $R_1$ and $R_2$ substituents to be in more than one steric position, they may be in either the $\alpha$ or $\beta$ position. It is of course understood that the basic sterol structure may contain substituents that do not adversely effect the properties of the compound at positions other than those of $R_1$, $R_2$, and $R_3$.

63 Claims, No Drawings

15-OXYGENATED STEROL COMPOUNDS AND THE USE OF SUCH COMPOUNDS TO INHIBIT THE BIOSYNTHESIS OF STEROLS

FIELD OF INVENTION

The present invention relates to certain 15-oxygenated sterol compounds, to pharmaceutical compositions containing certain 15-oxygenated sterol compounds, and to the use of these compounds to inhibit the biosynthesis of mevalonic acid, including all effects derived from inhibition of biosynthesis of mevalonic acid. Effects derived from inhibition of the biosynthesis of mevalonic acid include supression of the biosynthesis of sterols with a resultant reduction in serum cholesterol levels, in animals, and the inhibition of microorganism and cell growth. The 15-oxygenated sterols of the present invention are also effective to suppress appetite, which effect is believed to be related to their inhibitory activity on the biosynthesis of mevalonic acid and products derived therefrom, most especially cholesterol.

BACKGROUND OF THE INVENTION

In many instances the suppression of biosynthesis, either in vivo or in vitro, of sterols is desirable. For example, it is often desirable to suppress the formation of the sterol cholesterol in animals, including humans, whereby the serum cholesterol level in the animal will be lowered.

The concentration of cholesterol in blood serum has been correlated with a number of diseases, particularly atherosclerosis. Atherosclerosis is a condition marked by the formation of plaques in the arterial system. Cholesterol and cholesterol esters are major components of these plaques. While the etiology of the disease is not completely known, it appears that an elevated serum cholesterol level contributes to the development and the progression of atherosclerosis.

Cholesterol in animals is derived from two sources, first the intake and absorption of dietary cholesterol and second the biosynthesis of cholesterol from acetates by cells of various organs of the body, e.g., liver, intestines, and skin. The biosynthesis of cholesterol and other sterols from acetate in the body involves a complex sequence of reactions, one of which is the conversion of 3-hydroxy-3-methylglutaryl Coenzyme A into mevalonic acid. This reaction is considered to be a major regulation point in the normal biosynthesis of cholesterol in cells. If the biosynthesis of mevalonic acid can be inhibited in vivo, production of sterols is reduced, and serum cholesterol levels can thereby be lowered.

In British Pat. No. 860,303 certain aryloxy carboxylic acid esters, such as the methyl ester of 2-(4'-chlorophenoxy)-isobutyric acid, are proposed for use in suppressing blood cholesterol levels. While this compound has acquired significant importance in the clinical treatment of humans, for various reasons it is not as effective as is desired. Accordingly, more effective compounds for suppressing serum cholesterol levels are of great interest and importance.

Obesity is also a serious health problem. The correlation between excess weight and a number of diseases, particularly cardiovascular diseases, is well-known. Many peple, often for psychological or other reasons, find it difficult or impossible to adhere to weight control or weight loss diets. For this reason, techniques for safely and effectively suppressing appetite are greatly needed.

In accordance with the present invention it has been discovered that certain 15-oxygenated sterols, many of which are novel compounds, are effective in the inhibition of the biosynthesis of mevalonic acid and of sterols. A number of desirable effects can be derived from the inhibition of the biosynthesis of mevalonic acid, including suppressing the formation of cholesterol in animals, whereby serum cholesterol levels may be lowered.

In addition, the growth and proliferation of the cells of higher organisms and certain microorganisms, such as yeast and fungi, involve the formation of sterols. Accordingly, inhibition of the biosynthesis of mevalonic acid, and thus reducing sterol formation, is effective to inhibit the growth of cells, both normal and tumorous. Furthermore, inhibition of the biological synthesis of sterols has the effect of inhibiting the growth of certain microorganisms, thereby combatting fungal and yeast infections.

In addition to its role in sterol biosynthesis, mevalonic acid is an important precursor of a number of other important constituents of cells. Thus, while bacteria are generally considered to not contain or need sterols, their growth and proliferation requires synthesis of mevalonic acid and the products derived therefrom. Accordingly, inhibition of mevalonic acid biosynthesis should inhibit bacterial growth.

It has also been found, in accordance with the present invention, that the 15-oxygenated sterols and their derivatives are effective to suppress appetite. While the mechanism by which the 15-oxygenated sterols function to suppress appetite is not known, it is believed that this effect is in some way related to the mevalonic acid or sterol biosynthesis inhibiting activity of the 15-oxygenated sterols.

SUMMARY OF THE INVENTION

In accordance with the present invention, a method of inhibiting the biosynthesis of mevalonic acid, including all effects derived therefrom, is provided. The method comprises administering to a host of mevalonic acid biosynthesis inhibiting 15-oxygenated sterols. As used herein, the expression "15-oxygenated sterols" refers to sterols having oxygenated functions at the 3 and 15 position.

Suitable 15-oxygenated sterols, which are administered in amounts effective to inhibit biosynthesis of mevalonic acid, have the structural formula:

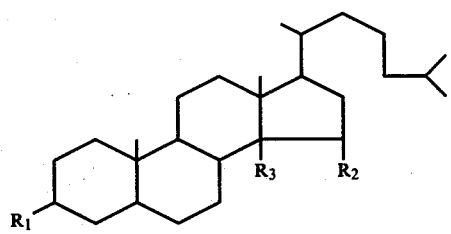

where:
$R_1$ is $-OH$, $=O$, $-OR_4$,

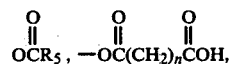

$OCR_5$, $-OC(CH_2)_n COH$, a sulfate group, or a Mg, Na, or K salt of a sulfate group;

$R_2$ is —OH, =O, or

—OCR$_5$;

$R_3$ is $\alpha$H, $\beta$H or an $\alpha$C$_1$ to C$_6$ alkyl group;
$R_4$ is a C$_1$ to C$_6$ alkyl group and preferably a C$_1$ to C$_3$ alkyl group;
$R_5$ is a C$_1$ to C$_{20}$ aliphatic group, a substituted C$_1$ to C$_{20}$ aliphatic group, or a phenyl group; and
n is a whole number from 2 to 6 and preferably from 2 to 4.

The basic ring structure may be saturated or unsaturated, and preferably there is a double bond between either the 7 and 8 or 8 and 14 carbon atoms. When there is a double bond between the 8 and 14 carbon atoms, there is no $R_3$ substituent. When it is possible for the $R_1$ and $R_2$ substituents to be in more than one steric position, they may be in either the $\alpha$ or $\beta$ position. It is of course understood that the basic sterol structure may contain substituents that do not adversely effect the properties of the compound at positions other than those of $R_1$, $R_2$ and $R_3$.

The present invention also pertains to pharmaceutical compositions, and the use of such compositions, comprising a pharmaceutically acceptable carrier in combination with a non-toxic but effective amount of a 15-oxygenated sterol of the type described above. These pharmaceutical compositions may be used to inhibit the biosynthesis of mevalonic acid, and derived effects of the inhibition of biosynthesis of sterols, such as inhibiting the cell growth and suppressing serum cholesterol. These pharmaceutical compositions may also be employed to suppress appetite.

The present invention also provides novel 15-oxygenated sterols having the structural formula:

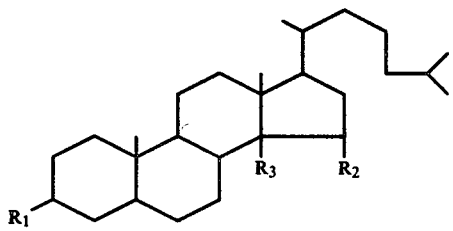

where:
$R_1$ is —OH, =O, —OR$_4$,

OCR$_5$, —OC(CH$_2$)$_n$COH, a sulfate group, or a Mg, Na, or K salt of a sulfate group;
$R_2$ is —OH, =O,

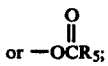
or —OCR$_5$;

$R_3$ is $\alpha$H, $\beta$H, or an $\alpha$C$_1$ to C$_6$ alkyl group;
$R_4$ is a C$_1$ to C$_6$ alkyl group;
$R_5$ is a C$_1$ to C$_{20}$ aliphatic group, a substituted C$_1$ to C$_{20}$ aliphatic group, or a phenyl group; and
n is a whole number from 2 to 6, with said $R_1$ and $R_2$ substituents, other than when they are=O, being in either the $\alpha$ or $\beta$ position, provided that when there is a double and bond between 8 and 14 and $R_1$ is —OH, $R_2$ is not —OH; when $R_3$ is $\alpha$ methyl and $R_1$ is —OH, $R_2$ is not —OH; when $R_3$ is $\alpha$methyl and $R_1$ is —OCH$_3$, $R_2$ is not =O or —OH; and when $R_1$ and $R_2$ are —OH, there is no —OH group attached to the 7 carbon atom.

DESCRIPTION OF THE PREFERRED EMBODIMENT

The 15-oxygenated sterols of the present invention may be prepared by a number of different synthesis techniques, depending on the particular sterol desired. Useful intermediates for preparing the sterols of the present invention are 3$\beta$-benzoyloxy compounds having the general formula:

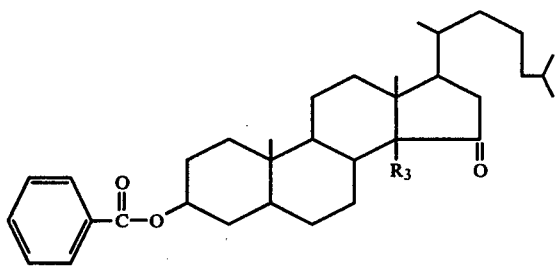

Such 3$\beta$-benzoyloxy compounds can be converted to corresponding 3$\beta$-hydroxy compounds by hydrolysis. Reduction, as with lithium aluminum hydride yields 3$\beta$,15-diols.

Another useful intermediate in preparing the 15-oxygenated sterols of the present invention are 3$\beta$-benzoyloxy, 14$\alpha$,15$\alpha$ epoxy compounds having the general formula:

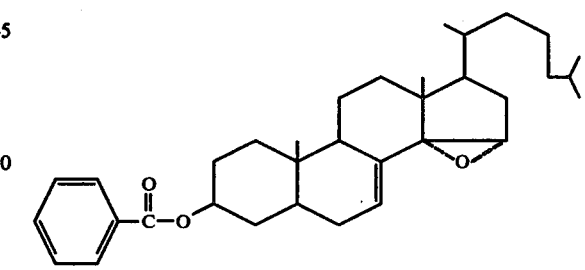

These compounds may be reacted with a reducing agent to yield the corresponding 3$\beta$,15$\alpha$-diols.

The 15-oxygenated sterol compounds of the present invention can be administered either as they are or in administration unit forms in combination with conventional pharmaceutical carriers. Suitable administration unit forms depend somewhat on the particular effect sought to be achieved with the sterols.

Typical administration unit forms include such oral administration forms as tablets, capsules, powders, granules, and oral solutions. Other administration unit forms include sublingual and buccal administration forms, topical application forms, and parenteral administration forms useful for subcutaneous, intramuscular, or intravenous administration.

If desired, the 15-oxygenated sterols can be conveniently made-up in dosage unit forms suitable for the particular mode of administration, with the quantity of active ingredient of each dosage unit being such that one or more units are required for each therapeutic administration. Each dosage unit preferably contains from about 5 mg to about 1000 mg of active 15-oxygenated sterol compound.

The dosage of active 15-oxygenated sterol necessary to obtain a desired effect is variable over a wide range, depending somewhat upon the nature of the particular 15-oxygenated sterol administered, the effect desired and the mode of administration. Typically, a suitable dosage is from about 0.1 mg to about 140 mg of active 15-oxygenated sterol per kg of body weight per day. Typically a suitable dose would be administered from 1 to 4 times a day.

Suitable pharmaceutical carriers which can be used to formulate administration units are well-known in the art. For example, if the 15-oxygenated sterol is to be administered in the form of a solid composition such as a tablet, the active 15-oxygenated sterol may be mixed with a pharmaceutical vehicle such as gelation, starch, lactose, magnesium stearate, talc, gum arabic, or the like. Tablets may be coated with sucrose, or with other agents, using known techniques, in order to delay disintegration in the stomach and thus provide a sustained action over an extended period of time.

Capsule preparations may be obtained by mixing the active 15-oxygenated sterols with an inert pharmaceutical filler or diluent and filling the resultant mixture into a rigid gelatin capsule or into a soft capsule. A syrup or elixir preparation may contain the active 15-oxygenated sterols together with a sweetening agent such as sucrose, antiseptic compounds, and/or suitable colorants.

Topical preparations may be prepared by mixing the active 15-oxygenated sterols with suitable salve and ointment bases. Typically such bases are polyvinyl alcohol, waxy polyethylene glycol, etc., or other nontoxic lipophilic agents or vehicles.

A parenteral liquid may be prepared by dissolving or suspending the active ingredient in a sterile liquid vehicle, such as water or brine, a non-volatile liquid polyethylene glycol, or an oil of vegetable or animal origin, e.g., cod liver oil, olive oil, etc. Parenteral liquids may also advantageously incorporate known lubricants, bactericides and fungicides, tonicity adjusting agents, local anesthetics, stabilizers, etc.

The mechanism by which the active 15-oxygenated sterols of the present invention function is not entirely understood. However, it has been shown that the active compounds inhibit the biosynthesis of sterols from acetate, but do not inhibit the biosynthesis of sterols from mevalonic acid. Since mevalonic acid is an essential intermediate in the biochemical pathway by which sterols are formed from acetates, it is clear that the 15-oxygenated sterols inhibit mevalonic acid formation.

It is known that one step in the biosynthesis of sterols from acetate involves conversion of 3-hydroxy-3-methylglutaryl Coenzyme A (HMG-CoA) to mevalonic acid. The rate of this reaction is controlled by the enzyme HMG-CoA reductase. It is believed that the 15-oxygenated sterols of the present invention function by affecting HMG-CoA reductase in some manner, either by depressing its activity or by limiting the amount of it in the system through destruction or suppression of its formation.

Constantly proliferating cells, such as those of the epidermis, developing brain, crypts of the intestinal mucosa, and spontaneous tumors, synthesize cholesterol at relatively high rates in vivo. Cells in interphase, such as those of muscle and the mature brain, do not. Tests with cultured cells demonstrate that cell division in vitro also requires cholesterol synthesis. Accordingly, inhibition of cholesterol formation, by blocking the biosynthesis of mevalonic acid, affects replication, in vivo, of cells that are normally in a proliferating state. Of course, suppression of cholesterol formation through blocking biosynthesis of mevalonic acid, also has the effect of lowering serum cholesterol levels.

The following examples further illustrate preferred embodiments of the present invention, including preferred embodiments of techniques for synthesizing various active 15-oxygenated sterols. The following examples also illustrate the effect of 15-oxygenated sterols in inhibiting biosynthesis of sterols, including in vivo inhibition in rats with a resultant reduction in serum cholesterol levels. These examples should in no way be considered limiting, but are merely illustrations of various features of the present invention.

EXAMPLE 1

Preparation of 5α-cholest-8(14)-en-3β-ol-15-one

3β-Benzoyloxy-5α-cholest-8(14)-en-15-one was prepared according to the technique of Knight et al., J. Biol. Chem., Vol. 241, p. 1502 (1966). The melting point, infra-red spectrum, elemental analysis, and mass spectrum of the product confirm its structure. The product showed a single component on thin-layer chromatographic analyses in three different systems.

The 3β-Benzoyloxy-5α-cholest-8(14)-en-15-one (1.0 g) was dissolved in ethanol (350 ml). Water (20 ml) and concentrated sulfuric acid (60 ml) were successively added and the resulting mixture was heated under reflux for 12 hours, cooled, reduced to ½ of its volume under reduced pressure, and diluted with 0.5 M NaCl solution (1,000 ml). The resulting precipitate was collected and recrystallized twice from acetone-methanol-water.

The crystals were dissolved in acetone and warmed in the presence of Norite A for 15 min. The solution was filtered through Hyflo Super-Cel (Johns-Manville Corp.) and the Super-Cel was washed with methanol (twice the volume of acetone). The acetone and methanol solutions were combined and, after the addition of water, 660 mg. (83% yield) of a crystalline product formed with was collected and dried in vacuo. The product was 5α-cholest-8(14)-en-3β-ol-15-one having the formula:

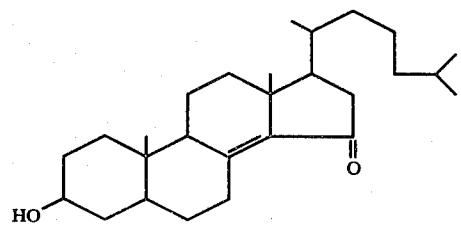

The structure of the product was confirmed by infrared (i.r.), ultraviolet spectral (u.v.), nuclear magnetic resonance spectral (n.m.r.), and mass spectral (m.s.)

analyses. The compound showed a single component on thin-layer chromatographic analyses on silica gel G plates using solvent systems comprising 10% ether in benzene and 35% ethyl acetate in chloroform.

EXAMPLE 2

Preparation of 5α-cholest-8(14)-en-3β,15-diols

3β-Benzoyloxy-cholest-8(14)-en-15-one (3.97 mmole) in ether (104 ml) was reduced with lithium aluminum hydride (16 mmole) for two hours at room temperature. The excess reagent was decomposed by the successive addition of ethyl acetate, a saturated solution of ammonium chloride, and water. Extraction with ether yielded 2.6 g of material which was subject to chromatography on an activated silicic acid column (75×3 cm).

Using benzene-ether (90:10) as the eluting solvent, fractions 25 ml in volume were collected. 672 mg. of one epimeric diol, designated diol A, eluted in fractions 250 through 375. After recrystallizing four times from acetonewater, one component was observed upon thin-layer chromatographic analysis in three different systems. 930 mg. of a second epimeric diol, designated diol B, eluted in fractions 425 through 650. After recrystallizing three times from acetone-water, the compound showed a single component upon thin-layer chromatographic analysis in three different systems.

Elemental, i.r., u.v., n.m.r., m.s., and x-ray crystallographic analyses confirm that diols A and B have the following structure, with the 15-hydroxy group of diol A being in the α position, and the 15-hydroxy group of diol B being in the β position:

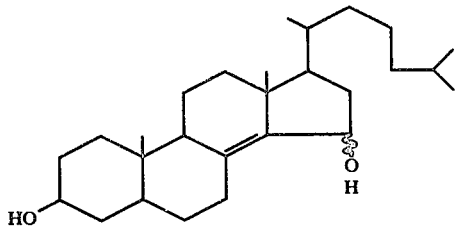

EXAMPLE 3

Preparation of 5α,14β-cholest-7-en-3β,15-diols

Treatment of 3β-benzoyloxy-cholesta-5,7-diene with HCl gas in chloroform, according to the technique of Knight et al. *J. Biol. Chem.*, Vol. 241, p. 1502 (1966), gave a product (70% yield) which melted at 148°–150° C. and contained a mixture of two isomers. Analysis by n.m.r. indicated the sample to contain approx. 73% 3β-benzoyloxy-5α-cholesta-7,14-diene.

This material (75 g; 148 mmol) was dissolved in anhydrous ether (3000 ml) with gentle warming on a steam bath. The solution was placed in an ice bath and cooled to 18° C. at which time a solution of m-chloroperbenzoic acid (63.6 g) in ether (400 ml) was added. The stirred mixture was allowed to stand at 0° C. for 5 hours and then at − 15° C. for 24 hours. The material which precipitated was collected on a filter, washed with cold ether, and recrystallized from acetone-water to give 3β-benzoyloxy-14α,15α-epoxy-5α-cholest-7-ene (40.2 g; 52% yield) having the structural formula:

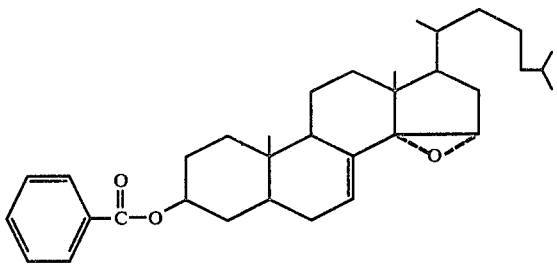

The structure of this compound was confirmed by i.r., n.m.r., and m.s. analyses. The compound showed a single component on thin-layer chromatographic (TLC) analyses on silica gel G plates (solvent systems: 35% ethyl acetate in chloroform and 10% ether in benzene).

The 3β-benzoyloxy-14α,15α-epoxy-5α-cholest-7-ene (2.0 g; 3.96 mmol) was dissolved in dry tetrahydrofuran (20 ml). Dry ether (200 ml) was added and the solution was cooled to 0° C. Boron trifluoride-etherate (20 ml) was slowly added with stirring. After standing at 0° C. for 30 min with occasional stirring, the mixture was poured into water and thoroughly extracted with ether. The combined extracts were dried over anhydrous magnesium sulfate, filtered, and evaporated to dryness under reduced pressure.

The residue (1.96 g) so obtained was subjected to chromatography on a silica gel column using increasing concentrations (0.5, 7.5 and 10%) of ether in benzene as the eluting solvent. Fractions of 24 ml in volume (16 min per fraction) were collected. The contents of fractions 70–100 were pooled and the residue obtained upon evaporation of the solvent was recrystallized from acetone-water to yield 3β-benzoyloxy-5α, 14β-cholest-7-en-15-one (860 mg; 43% yield). The structure of this intermediate was confirmed by i.r., n.m.r., and m.s. analyses. The compound showed a single component on TLC analyses on silica gel G plates (solvent systems: 35% ethyl acetate in chloroform, 10% ether in benzene, and benzene).

The 3β-benzoyloxy-5α,14β-cholest-7-en-15-one (2.33 g; 4.62 mmol) was dissolved in anhydrous ether (150 ml) and lithium aluminum hydride (2.80 g; 73.9 mmol) was added and the resulting mixture was stirred at 25° C. for 1 hour. After cooling the mixture to 0° C., ice was cautiously added to decompose the excess hydride. The mixture was poured into 0.34 M aqueous sodium chloride and thoroughly extracted with ether containing methylene chloride (5%). The combined extracts were dried over anhydrous magnesium sulfate and evaporated to dryness under reduced pressure to yield a white solid (1.80 g).

Preparative thin-layer chromatography on silica gel PF (1 mm thickness; solvent, 20% ether in benzene; developed twice) indicated two components ($R_f$ 0.22 and 0.34). The component of $R_f$ 0.22 was extracted with warm chloroform, filtered, and recrystallized from acetone-water to give 5α,14β-cholest-7-en-3β,15β-diol (1.51 g; 81% yield).

The component of $R_f$ 0.34 from the preparative thin-layer chromatography was eluted with warm chloroform and, upon crystallization from acetone-water, yielded 5α,14β-cholest-7-en-3β,15α-diol (167 mg; 9% yield).

Both compounds showed a single component on TLC analyses on silica gel G plates (solvent systems: 35% ethyl acetate in chloroform and 10% ether in benzene). The structure of both compounds was confirmed by x-ray crystallographic, i.r., n.m.r., and m.s. analyses as:

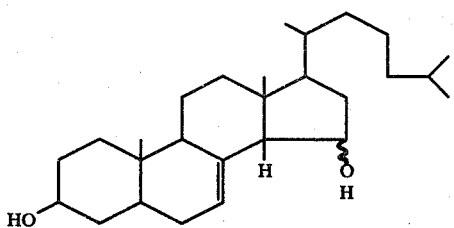

EXAMPLE 4

Preparation of 14α-Methyl-5α-cholest-7-en-3β-ol-15-one

3β-Benzoyloxy-14α-methyl-5α-cholest-7-en-15-one was prepared according to the technique of Knight et al., *J. Biol. Chem.*, Vol. 241, p. 1502 (1966). To 1.00 g (1.92 mmol) of this material in ethanol (190 ml) was added potassium hydroxide (4.0 g) in water (5 ml). The resulting mixture was heated under reflux for 1.5 hours under nitrogen. After reduction of the volume to approximately ⅓ the initial volume, the mixture was poured into 0.86 M sodium chloride (1,000 ml) and thoroughly extracted with ether containing methylene chloride (5%). The combined ether extracts were dried over anhydrous magnesium sulfate and evaporated to dryness under reduced pressure. The resulting residue was crystallized from methanol-water to yield 14α-methyl-5α-cholest-7-en-3β-ol-15-one (0.760 g; 95% yield) having the formula:

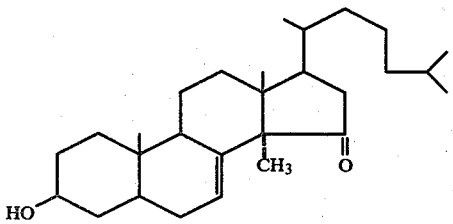

The structure of the compound was confirmed by i.r., n.m.r., and m.s. analyses. The compound showed a single component on thin-layer chromatographic analyses on silica gel G plates (solvent systems: 10% ether in benzene, 35% ethyl acetate in chloroform, and 10% ether in hexane) and on gas-liquid chromatographic analyses on 3% OV-1 and 3% OV-17 columns (column temperature, 270° C.).

EXAMPLE 5

Preparation of 14α-methyl-5α-cholest-7-en-3β,15-diols

3β-Benzoyloxy-14α-methyl-cholest-7-en-15-one was prepared following the technique of Knight et al, *J. Biol. Chem.*, Vol. 241, p. 1502 (1966). 100 mg. of this material was reduced with 200 mg. lithium aluminum hydride at room temperature for 12 hours. The excess reagent was decomposed by the addition of ethyl acetate. Water was added and the resulting mixture was extracted with ether.

The oily residue obtained upon evaporation of the solvent was subjected to chromatography on an activated silicic acid column. Using benzene-ether (90:10) as the eluting solvent, fractions 16 ml. in volume were collected. 26 mg. of one diol, designated Diol A, was eluted in fractions 9-13 and recrystallized from ethyl acetate yielding 18 mg. 46 mg. of a second diol, designated Diol B, was eluted in fractions 18-30 and recrystallized from ethyl acetate yielding 26 mg.

Elemental, m.s., n.m.r., and x-ray crystallographic analyses confirmed that the diols had the following structural formula, with the 15-hydroxy group of diol A being in the β position and the 15-hydroxy group of Diol B being in the α position:

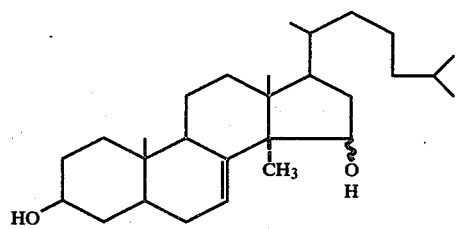

EXAMPLE 6

Preparation of 14α-Ethyl-5α-cholest-7-en-3β-ol-15-one and 3β-ethoxy-14α-ethyl-5α-cholest-7-en-15-one 5α-Cholest-8(14)-en-3β-ol-15-one (10.0 g; 24.9 mmol), prepared as in Example 1, was added to a stirred solution of potassium t-butoxide, prepared by dissolving potassium metal (17.3 g) in t-butyl alcohol (819 ml). Ethyl iodide (127.4 ml) was added in one portion to the reaction mixture and stirring was continued for 1.75 hours. The volume of the reaction mixture was reduced to about ⅓ of the initial volume under reduced pressure. Water was added and the resulting mixture was thoroughly extracted with ether. The combined extracts were dried over anhydrous magnesium sulfate and evaporated to dryness under reduced pressure. The resulting residue was subjected to medium pressure (60 p.s.i.) liquid chromatography using a silica gel (0.032-0.063 mm) column (100 cm × 2.5 cm). Using 10% ether in benzene as the eluting solvent, fractions 20 ml in volume (flow rate, 5 ml per min) were collected.

The contents of fractions 75 through 88 were pooled and, after evaporation of the solvent under reduced pressure, crystallized from acetone-water to give 14α-ethyl-5α-cholest-7-en-3β-ol-15-one (4.5 g; 42.2% yield) having the structural formula:

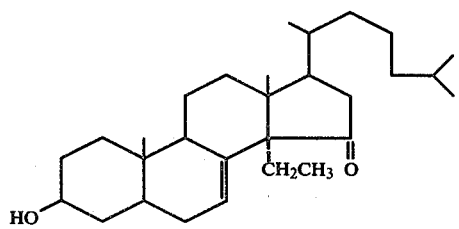

The structure of compound was confirmed by i.r., n.m.r., and m.s. analyses. The compound showed a single component on thin-layer chromatographic analyses on silica gel G plates using solvent system comprising 10% ether in benzene and 35% ethyl acetate in chloroform and on gas-liquid chromatographic analyses on 3% OV-1 and 3% OV-17 columns (column temperature, 250° C.).

The contents of fractions 25 through 29 from the medium pressure silica gel column chromatography were pooled and, after evaporation of the solvent under reduced pressure, crystallized from acetone-water to give 3β-ethoxy-14α-ethyl-5α-cholest-7-en-15-one (2.1 g; 18.5% yield) having the structural formula:

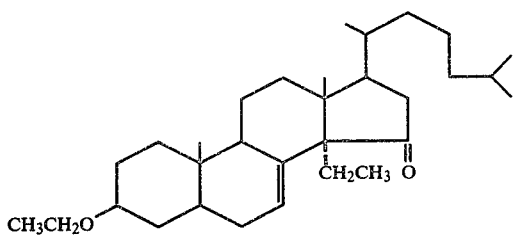

The structure of the product was confirmed by i.r., n.m.r., and m.s. analyses. The compound showed a single component on thin-layer and gas-liquid chromatographic analyses using the techniques described above for 3β-ethoxy-14α-ethyl-5α-cholest-7-en-15-one.

EXAMPLE 7

Preparation of
Bis-3β,15α-acetoxy-14α-ethyl-5α-cholest-7-ene and
3β-Acetoxy-14α-ethyl-5α-cholest-7-en-15β-ol To 14α-ethyl-5α-cholest-7-en-3β-ol-15-one (2.0 g; 4.6 mmol), prepared as in Example 6, in ether (300 ml) was added lithium aluminum hydride (3.0 g; 79.1 mmol). After stirring for 2 hours at room temperature, the reaction mixture was cooled to 0° C. and ice was cautiously added to decompose the unreacted hydride. The resulting mixture was poured into a 0.34 N sodium chloride solution and extracted thoroughly with ether containing methylene chloride (5%). The combined ether extracts were dried over anhydrous magnesium sulfate and evaporated to dryness under reduced pressure. The residue (1.92 g) was crystallized from acetone-water to give a white solid (1.89 g; 94.5% yield).

The crystallized material was subjected to medium pressure (100 p.s.i.) liquid chromatography using a silica gel (0.032–0.063 mm) column (118 cm×1.5 cm). Using 10% ether in benzene as the eluting solvent, fractions 20 ml in volume (flow rate, 5 ml per min) were collected. The contents of fractions 54 through 78 were pooled and, after evaporation of the solvent, crystallized from acetone-water to give a white solid (1.78 g; 89%) which melted at 171°–173° C. This material appeared to be a mixture of 14α-ethyl-5α-cholest-7-en-3β,15α-diol (70%) and 14α-ethyl-5α-cholest-7-en-3β,15β-diol (30%).

No resolution of the two epimers could be observed on thin-layer chromatographic analyses on silica gel G plates using 3 different solvent systems (10% ether in benzene, 20% ethyl acetate in petroleum ether, and 35% ethyl acetate in chloroform) or on gas-liquid chromatography of the free sterols on 3% OV-1 or 3% OV-17 columns (column temperature, 270° C.).

To the epimeric mixture (2.00 g; 4.65 mmol), obtained as described above, in pyridine (15 ml) was added acetic anhydride (15 ml). After standing at room temperature for 24 hours under nitrogen, the mixture was poured into water and thoroughly extracted with ether containing methylene chloride (5%). The combined ether extracts were successively washed with water, cold aqueous HCl (5%), aqueous sodium carbonate (5%), and water. The resulting ether solution was dried over anhydrous magnesium sulfate and evaporated to dryness under reduced pressure to obtain a white residue (2.34 g).

The white residue, which showed two major components and two trace components on thin-layer chromatographic analysis on a silica gel G plate (solvent, benzene), was subjected to medium pressure (60 p.s.i.) liquid chromatography using a silica gel (0.032–0.063 mm) column (100 cm ×2.5 cm). Using 1.25% ether in benzene as the eluting solvent, fractions 20 ml in volume (flow rate, 5 ml per min) were collected.

The contents of fractions 41 through 58 were pooled and, after evaporation of the solvent, crystallized from acetone-water to give bis-3β,15α-acetoxy-14α-ethyl-5α-cholest-7-ene (1.31 g; 54.8% yield) having the formula:

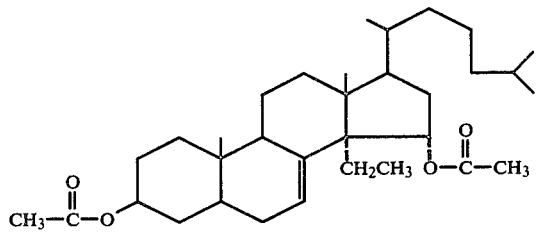

The structure of the product was confirmed by i.r.,n.m.r., and m.s. analyses. The compound showed a single component on thin-layer chromatographic analyses on silica gel G plates (solvent systems: benzene, 10% ether in benzene, 10% ether in hexane, and 35% ethyl acetate in chloroform) and on gas-liquid chromatographic analyses on 3% OV-1 and 3% OV-17 columns (column temperature, 270° C.).

The contents of fractions 72 through 90 of the medium pressure liquid chromatography were pooled and, after evaporation of the solvent, crystallized from acetone-water to give 3β-acetoxy-14α-ethyl-5α-cholest-7-en-15β-ol (0.46 g; 20.9% yield) having the structure:

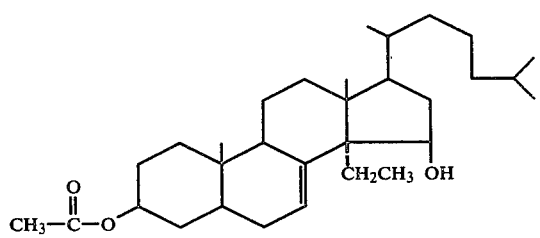

The structure was confirmed by i.r.,n.m.r., and m.s. analyses. The compound showed a single component on thin-layer chromatographic analyses on silica gel G plates (solvent systems: benzene, 10% ether in benzene, 10% ether in hexane, and 35% ethyl acetate in chloroform) and on gas-liquid chromatographic analyses on 3% OV-1 and 3% OV-17 columns (column temperature, 270° C.).

EXAMPLE 8

Preparation of 14α-Ethyl-5α-cholest-7-en-3β,15β-diol

3β-Acetoxy-14α-ethyl-5α-cholest-7-en-15β-ol (0.50 g; 1.06 mmol), prepared as in Example 7, in ether (50 ml) was reduced with lithium aluminum hydride (1.00 g; 0.97 mml) for 2 hours. The resulting reaction mixture was processed following the technique described in Example 7 for the recovery of the 3β,15 diols to give a white solid (0.44 g). Upon crystallization of the white solid from acetone-water, 14α-ethyl-5α-cholest-7-en-3β,15β-diol (0.42 g; 93% yield) was recovered. Analyses by i.r.,n.m.r., and m.s. confirm that the product has the structural formula:

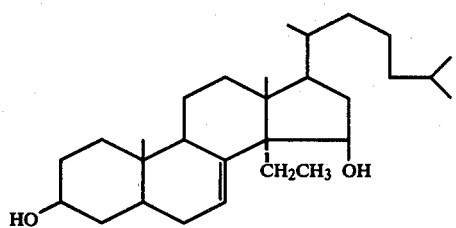

The compound showed a single component on thin-layer chromatographic analyses on silica gel G plates (solvent system: 10% ether in benzene, 35% ethyl acetate in chloroform) and on gas-liquid chromatographic analysis of the bis-3β,15β-trimethylsiloxy-derivative on 3% OV-1 and 3% OV-17 columns (column temperature, 250° C.).

EXAMPLE 9

Preparation of
3β-Methoxy-14α-methyl-5α-cholest-7-en-15-one

3β-Benzoyloxy-5α-cholest-8(14)-en-15-one (11.0 g; 21.8 mmol) was added to a stirred solution of potassium t-butoxide, prepared by dissolving of potassium metal (18.4 g) in t-butyl alcohol (1,000 ml). After stirring at room temperature for 15 min, methyl iodide (110 ml) was added in one portion and stirring was continued for 12 hours. Water was added and the resulting mixture was thoroughly extracted with ether. The combined ether extracts were dried over anhydrous magnesium sulfate and evaporated to dryness under reduced pressure. The resulting residue was subjected to chromatography on an alumina column (400 g; neutral alumina, grade 1; 140 cm×2 cm). Using benzene as the eluting solvent, fractions 24 ml in volume (1.5 ml per min) were collected.

The contents of fractions 35 through 46 were pooled and the residue obtained after evaporation of the solvent under reduced pressure was crystallized from acetone-water to give 3β-methoxy-14α-methyl-5α-cholest-7-en-15-one (5.63 g; 60.3% yield) having the formula:

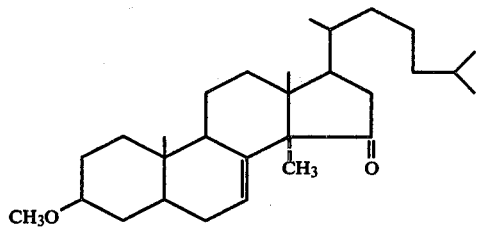

The structure of the compound was confirmed by i.r.,n.m.r., and m.s. analyses. The purity was in excess of 98% on the basis of gas-liquid chromatographic analyses on 3% OV-1 and 3% OV-17 columns (column temperature, 250° C.). In addition, the compound showed a single component on thin-layer chromatographic analyses on silica gel G plates (solvent systems: 10% ether in benzene, 10% ether in hexane, 35% ethyl acetate in chloroform, and 20% ethyl acetate in petroleum ether).

The contents of fractions 10 through 16 were pooled and the residue obtained upon evaporation of the solvent under reduced pressure was crystallized from chloroform-methanol to give 3β-benzoyloxy-14α-methyl-5α-cholest-7-en-15-one (1.65; 14.6% yield). The product showed a single component on thin-layer chromatographic analyses on silica gel G plates (solvent systems: benzene, 10% ether in benzene, and 10% ether in hexane).

EXAMPLE 10

Preparation of
3β-Methoxy-14α-methyl-5α-cholest-7-en-15β-ol and
3β-Methoxy-14α-methyl-5α-cholest-7-en-15α-ol Lithium aluminum hydride (2.0 g; 52.7 mmol) was added to a solution of 3β-methoxy-14α-methyl-5α-cholest-7-en-15-one (1.0 g; 2.33 mmol) in ether (100 ml). After stirring for one hour at room temperature, the reaction mixture was cooled to 0° C. and ice was cautiously added to decompose the untreated hydride. The resulting mixture was poured into a 0.34 N NaCl solution (300 ml) and thoroughly extracted with ether containing methylene chloride (5%). The combined ether extracts were dried over anhydrous magnesium sulfate and evaporated to dryness under reduced pressure to yield a colorless glass (0.95 g). This material was subjected to preparative thin-layer chromatography on silica gel-PF plates (1 mm thickness; solvent system, 10% ether in benzene). Two components of $R_f$ 0.36 and 0.24 were noted.

The less polar component ($R_f$ 0.36) was eluted from the plate with warm chloroform and gave, upon evaporation of the solvent, 3β-methoxy-14α-methyl-5α-cholest-7-en-15β-ol (410 mg; 40.8% yield) as a colorless glass. The more polar component ($R_f$ 0.24) was extracted from the plate with warm chloroform and gave, upon evaporation of the solvent, 3β-methoxy-14α-methyl-5α-cholest-7-en-15α-ol (272 mg; 27.1% yield) in the form of a colorless glass.

Both compounds showed a single component on thin-layer chromatographic analyses on silica gel G plates (solvent systems: 10% ether in benzene, 35% ethyl acetate in chloroform) and on gas-liquid chromatographic analyses on 3% OV-1 and 3% OV-17 columns (column temperature, 250° C.). Analyses by i.r.,n.m.r., and m.s. confirm the structure of the two compounds as:

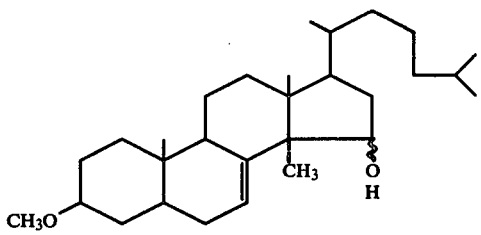

EXAMPLE 11

Preparation of 5α-Cholest-8(14)-en-3β, 7ε,15ε-triol

To 3β-benzoyloxy-14α,15α-epoxy-5α-cholest-7-ene (5.0 g; 9.91 mmol) in ethanol (810 ml) was added a solution of KOH (28 g) in water (90 ml) and the resulting mixture was heated under reflux for 5 hours. After reduction of the volume to about ¼ of the initial value under reduced pressure, the mixture was poured into cold water (1,000 ml).

The resulting precipitate (3.87 g) was collected and subjected to chromatography on a silica gel (130 g; 60-200 mesh) column (60 cm×2 cm). The column was eluted successively with chloroform (200 ml), a mixture of chloroform and ethyl acetate (1:1; 200 ml), and ethyl acetate. Fractions 20 ml in volume were collected.

Fractions 45 through 100, which contained the major product, were pooled and the solvent was evaporated under reduced pressure. The resulting residue was recrystallized from acetone-water to give 5α-cholest-8(14)-en-3β,7ε,15ε-triol (2.20 g; 53% yield) having the structure:

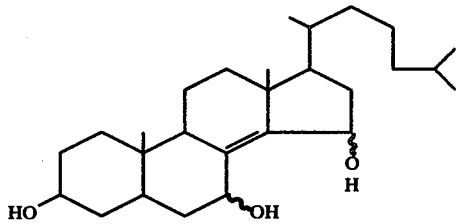

The structure of the compound was confirmed by i.r.,n.m.r. and m.s. analyses. The compound showed a single component on thin-layer chromatographic analyses on silica gel G plates (solvent systems: 35% ethyl acetate in chloroform and ethyl acetate). The tris-trimethylsilyl ether derivative of the compound showed a single component on gas-liquid chromatographic analyses on 3% OV-1 and 3% OV-17 columns (column temperature, 250° C.).

EXAMPLE 12

Preparation of 5α-Cholest-8(14)-en-3,7,15-trione.

To 5α-cholest-8(14)-en-3β,7ε,15ε-triol (300 mg; 0.72 mmol) in dry methylene chloride (60 ml) was added a suspension of pyridinium chlorochromate (1.10 g; 5.15 mmol) in dry methylene chloride (30 ml). The stirred reaction mixture was maintained under a nitrogen atmosphere for 30 min. and then poured into ether. The separated ether phase was washed successively with water, cold 5% HCl, 5% Na₂CO₃, and water. The ether solution was dried over anhydrous magnesium sulfate and evaporated to dryness under reduced pressure.

Portions of the resulting yellow residue (266 mg) were subjected to thin-layer chromatographic analyses of silica gel G plates which indicated one major component (solvent systems: 35% ethyl acetate in chloroform and 50% ethyl acetate in benzene). The product was subjected to medium pressure (60 p.s.i.) liquid chromatography using a silica gel (0.032–0.063 mm) column (118 cm×1.5 cm). Using 10% ethyl acetate in chloroform as the eluting solvent, fractions 20 ml in volume (flow rate, 5 ml per min) were collected. The contents of fractions 36 through 40 were pooled and, after evaporation of the solvent, crystallized from acetone-water to give 5α-cholest-8(14)-en-3,7,15-trione (170 mg; 57% yield) having the structure:

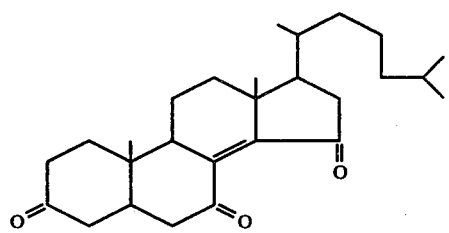

The structure was confirmed by i.r.,n.m.r., and m.s. analyses. The product showed a single component on gas-liquid chromatographic analysis on a 3% OV-1 column. A similar analysis on a 3% OV-17 column indicated the presence of a minor (~8%) impurity as a shoulder on the distal side of the major peak.

EXAMPLE 13

Preparation of 14α-Ethyl-5α-cholest-7-en-3β,15α-diol

To bis-3β,15α-acetoxy-14α-ethyl-5α-cholest-b 7-ene (1.00 g; 1.94 mmol) in ether (100 ml) was added lithium aluminum hydride (2.00 g; 52.7 mmol). After stirring for 3 hours at room temperature, the reaction mixture was cooled to 0° C. and ice was cautiously added to decompose the unreacted hydride. The mixture was poured into a 0.34 M sodium chloride solution and thoroughly extracted with ether containing methylene chloride (5%).

The combined ether extracts were dried over anhydrous magnesium sulfate and evaporated to dryness under reduced pressure. The resulting residue (0.79 g) was crystallized from acetone-water to give 14α-ethyl-5α-cholest-7-en-3β,15α-diol (0.76 g; 91.1% yield) having the formula:

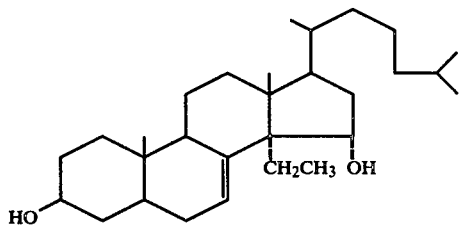

The structure of the compound was confirmed by i.r.,n.m.r., and m.s. analysis. The compound showed a single component on thin-layer chromatographic analyses on silica gel G plates (solvent systems; 10% ether in benzene, 35% ethyl acetate in chloroform) and on gas-liquid chromatographic analyses of the bis-3β,15α- trimethylsiloxy derivative on 3% OV-1 and 3% OV-17 columns (column temperature, 250°C.).

EXAMPLE 14

Preparation of 3β-Acetoxy-14α-n-propyl-5α-cholest-7-en-15-one

5α-Cholest-8(14)-en-3β-ol -15-one (10.0 g; 24.9 mmol) was added to a stirred solution of potassium t-butoxide, prepared by dissolving potassium metal (17.3 g) in t-butyl alcohol (819 ml; dried over Linde type 3A molecular sieve). n-Propyl iodide (140 ml) was added in one portion to the reaction mixture and stirring was continued for 4 hours. The volume of the reaction mixture was reduced to about ⅛ of the initial volume under reduced pressure. Water was added and the resulting mixture was thoroughly extracted with ether. The combined extracts were dried over anhydrous magnesium sulfate and evaporated to dryness under reduced pressure.

The resulting residue was subjected to medium pressure (60 p.s.i.) liquid chromatography using a silica gel (0.032–0.063 mm; 910 g) column (100 cm×2.5 cm). Using 5% ether in benzene as the eluting solvent, fractions 20 ml in volume (flow rate, 5 ml per min) were collected. The contents of fractions 102 through 192 were pooled and, after evaporation of the solvent under reduced pressure, crystallized from acetone-water to give crude 14α-n-propyl-5α-cholest-7-en-3β-ol-15-one (4.5 g; 41% yield) as a white crystalline solid melting at 119°–123° C.

While the product showed a single component on thin-layer chromatographic analyses on silica gel G plates in two different solvent systems (10% ether in benzene, 35% ethyl acetate in chloroform), gas-liquid chromatographic analyses on either a 3% OV-1 or 3% OV-17 column showed the pressure (about 10%) of a less polar component.

The crude 14α-n-propyl-5α-cholest-7-en-3β-ol-15-one (0.5 g; 11.3 mmol) was dissolved in dry pyridine (50 ml) and acetic anhydride (50 ml) was added. After standing at room temperature for 24 hours under nitrogen, the reaction mixture was poured into water. The resulting mixture was thoroughly extracted with ether containing methylene chloride (5%). The combined extracts were washed successively with water, cold aqueous HCl, aqueous sodium carbonate (5%), and water. The resulting ether solution was dried over anhydrous magnesium sulfate and evaporated to dryness under reduced pressure.

The resulting white solid (5.2 g) was subjected to medium pressure (60 p.s.i.) liquid chromatography using a silica gel (0.032–0.063 mm; 910 g) column (100 cm×2.5 cm). Using benzene as the eluting solvent, fractions 20 ml in volume (flow rate, 5 ml per min) were collected. The contents of fractions 130 through 178 were pooled and, after evaporation of the solvent under reduced pressure, crystallized from acetone-water to yield 3β-acetoxy-14α-n-propyl-5α-cholest-7-en-15-one (4.1 g; 74% yield) in the form of white crystals melting at 110°–111°. The compound showed a single component on thin-layer chromatographic analyses on silica gel G plates (solvent systems: benzene, 10% ether in benzene, 10% ether in hexane, and 35% ethyl acetate in chloroform) and on gas-liquid chromatographic analyses on 3% OV-1 and 3% OV-17 columns (column temperature, 270°C.). Analyses by i.r.,n.m.r., and m.s. confirm the structure as:

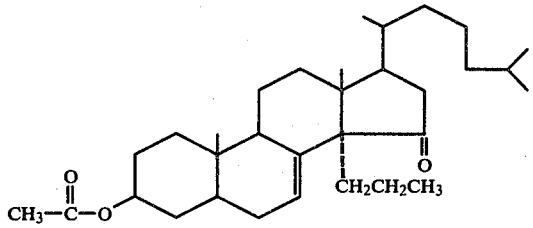

EXAMPLE 15

Preparation of 14α-n-Propyl-5α-cholest-7-en-3β-ol-15-one

3β-Acetoxy-14α-n-propyl-5α-cholest-7-en-15-one (300 mg; 0.62 mmol) was dissolved in absolute ethanol (63.4 ml) and 7.14 N KOH (3.35 ml) was added. The resulting mixture was heated under reflux for 2 hours under nitrogen and, after reduction in volume to about ½ its initial value under reduced pressure, was poured into water. The mixture was thoroughly extracted with ether containing methylene chloride (5%) and the combined extracts were dried over anhydrous magnesium sulfate and evaporated to dryness under reduced pressure.

The resulting white solid was crystallized from acetone-water to give 14α-n-propyl-5α-cholest-7-en-3β-ol-15-one (264 mg; 96% yield) having the formula:

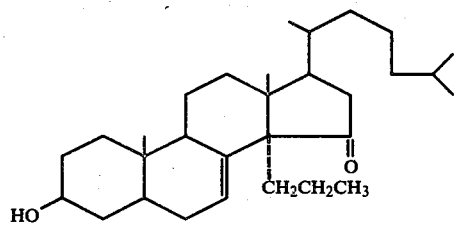

The structure was confirmed by i.r., n.m.r., and m.s. analyses. The compound showed a single component on thin layer chromatographic analyses on silica gel G plates (solvent systems: 10% ether in benzene, 10% ether in hexane (and 35% ethyl acetate in chloroform) and on gas-liquid chromatographic analyses of the free sterol and its trimethylsilyl ether derivative on 3% OV-1 and 3% OV-17 columns (column temperature, 270° C.).

EXAMPLE 16

Preparation of Bis-3β,15α-acetoxy-14α-n-propyl-5α-cholest-7-ene and 3β-Acetoxy-14α-n-propyl-5α-cholest-7-en-15β-ol To 14α-n-propyl-5α-cholest-7-en-3β-ol-15-one (3.0 g; 6.2 mmol) in ether (300 ml) was added lithium aluminum hydride (6.0 g; 158 mmol). After stirring for 2 hours at room temperature, the reaction mixture was cooled to 0° C. and ice was cautiously added to decompose the unreacted hydride. The mixture was poured into a 0.34 N sodium chloride solution and extracted thoroughly with ether containing methylene chloride (5%).

The combined ether extracts were dried over anhydrous magnesium sulfate and evaporated to dryness under reduced pressure. The residue (2.59 g) was crystallized from acetone-water to give a white solid (2.53 g; 93% yield) which melted at 104.5°–105.5°. This material appears to be a mixture of 14α-n-propyl-5α-cholest-7-en-3β,15α-diol (64%) and 14α-n-propyl-5α-cholest-7-en-3β,15β-diol (36%).

To a solution of the mixture of the epimeric diols (2.0 g; 4.50 mmol) in dry pyridine (15 ml) was added acetic anhydride (15 ml). After standing for 24 h at room temperature under nitrogen, the mixture was poured into water and thoroughly extracted with ether containing methylene chloride (5%). The combined ether extracts were washed successively with water, cold aqueous HCl (5%), aqueous sodium carbonate (5%), and water and dried over anhydrous magnesium sulfate. The residue (2.32 g) obtained upon evaporation of the solvent was subjected to medium pressure (60 p.s.i.) liquid chromatography using a silica gel (0.032–0.063 mm; 910 g) column (100 cm×2.5 cm). Using 1% ether in benzene as the eluting solvent, fractions 20 ml in volume (flow rate, 5 ml per min) were collected.

The contents of fractions 40 through 62 were pooled and, after evaporation of the solvent under reduced pressure, crystallized from acetone-water to give bis-3β,15α-acetoxy-14α-n-propyl-5α-cholest-7-ene (1.28 g; 53.8% yield) as a white crystalline solid melting at 128°–129°.

The compound showed a single component on thin-layer chromatographic analyses on silica gel G plates (solvent systems: benzene, 10% ether in benzene, 10% ether in hexane, and 35% ethyl acetate in chloroform) and on gas-liquid chromatographic analyses on 3% OV-1 and 3% OV-17 columns (column temperature, 270° C.). The following structure was confirmed by i.r., n.m.r., and m.s. analyses:

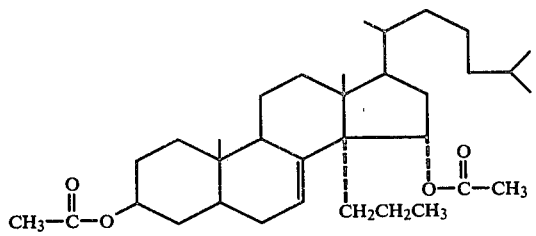

The contents of fractions 78 through 94 from the silica gel column were pooled and, after evaporation of the solvent under reduced pressure, crystallized from acetone-water to give 3β-acetoxy-14α-n-propyl-5α-cholest-7-en-15β-ol (0.48 g; 22% yield) melting at 103.5°–104.5°. By i.r., n.m.r., and m.s. analyses, the structure was confirmed as:

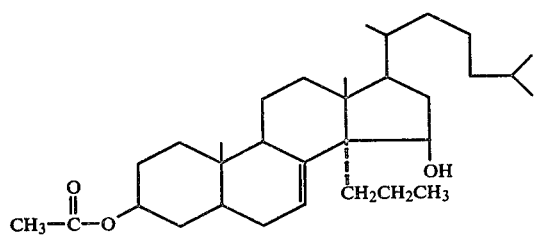

The compound showed a single component of thin-layer chromatographic analyses on silica gel G plates (solvent systems: benzene, 10% ether in benzene, 10% ether in hexane, and 35% ethyl acetate in chloroform) and on gas-liquid chromatographic analyses on 3% OV-1 and 3% OV-17 columns (column temperature, 270° C.).

EXAMPLE 17

Preparation of 14α-n-Propyl-5α-cholest-7-en-3β,15α-diol

To bis-3β,15α-acetoxy-14α-n-propyl-5α-cholest-7-ene (200 mg; 0.38 mmol) in ether (50 ml) was added lithium aluminum hydride (500 mg; 13.2 mmol). After stirring for 3 hours at room temperature, the reaction mixture was cooled to 0° C. and ice was cautiously added to decompose the unreacted hydride. The resulting mixture was poured into a 0.34 N sodium chloride solution and extracted thoroughly with ether containing methylene chloride (5%). The combined ether extracts were dried over anhydrous magnesium sulfate and evaporated to dryness under reduced pressure.

The residue (146 mg) so obtained was crystallized from acetone-water to give 14α-n-propyl-5α-cholest-7-en-3β,15α-diol (135 mg; 80.4% yield) having the formula:

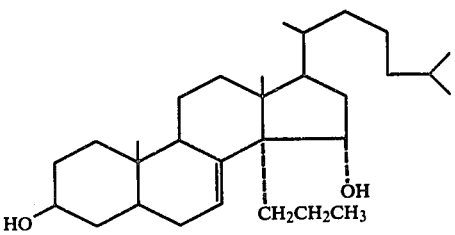

The structure was confirmed by i.r., n.m.r., and m.s. analyses. The compound showed a single component on thin-layer chromatographic analyses on silica gel G plates (solvent systems: 10% ether in benzene, chloroform, 35% ethyl acetate in chloroform) and on gas-liquid chromatographic analyses of the free sterol and its bis-3β,15α-trimethylsiloxy derivative on 3% OV-1 and 3% OV-17 columns (column temperature, 270° C.).

EXAMPLE 18

Preparation of 14α-n-Propyl-5α-cholest-7-en-3β,15β-diol

To 3β-acetoxy-14α-n-propyl-5α-cholest-7-en-15β-ol (200 mg; 0.41 mmol) in ether (50 ml) was added lithium aluminum hydride (500 mg; 13.2 mmol). After stirring for 3 hours at room temperature, the reaction mixture was cooled to 0° and ice was cautiously added to decompose the excess hydride. The resulting mixture was poured into a 0.34 N sodium chloride solution and extracted thoroughly with ether containing methylene chloride (5%). The combined ether extracts were dried over anhydrous magnesium sulfate and evaporated to dryness under reduced pressure.

The residue (152 mg) so obtained was crystallized from acetone-water to give 14α-n-propyl-5α-cholest-7-en-3β,15β-diol (145 mg; 79% yield) having the formula:

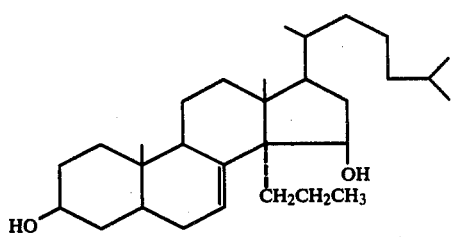

The structure of the compound was confirmed by i.r., n.m.r., and m.s. analyses. The compound showed a single component on thin-layer chromatographic analyses on silica gel G plates (solvent systems: 10% ether in benzene, chloroform, 35% ethyl acetate in chloroform) and on gas-liquid chromatographic analyses of the free sterol and its bis-3β,15α-trimethylsiloxy derivative on 3% OV-1 and 3% OV-17 columns (column temperature, 270° C.).

EXAMPLE 18A

Preparation of 3β-Hexadecanoyloxy-14α-ethyl-5α-cholest-7-en-15α-ol, 3β-Hexadecanoyloxy-14α-ethyl-5α-cholest-7-en-15β-ol, and bis-3β,15α-hexadecanoyloxy-14α-ethyl-5α-cholest-7-ene To a mixture of 14α-ethyl-5α-cholest-7-en-3β,15α-diol and 14α-ethyl-5α-cholest-7-en-3β,15β-diol (4.40 g; 10.2 mmol; ~70:30 mixture of the 15α- and 15β-hydroxy epimers as indicated by gas-liquid chromatographic analysis of the 3β-trimethylsiloxy derivative) in dry pyridine (22 ml) was added hexadecanoyl chloride (3.10 g; 11.3 mmol). The reaction mixture was heated under reflux for 1 hour under nitrogen and, after cooling to room temperature, poured into water.

The resulting mixture was thoroughly extracted with ether containing methylene chloride (5%). The organic phase was successively washed with water, cold 0.6 N HCl, 0.47 M Na2CO3, and water and dried over anhydrous magnesium sulfate. A portion of the white residue (5.35 g) obtained upon evaporation of the solvent was analyzed by thin-layer chromatography on a silica gel G plate (solvent, benzene). Three major components (R_f values of 0.20, 0.45, and 0.79) were noted. The mixture was subjected to medium pressure (60 p.s.i.) silica gel (0.032–0.063 mm; 910 g) column (100 cm×2.5 cm) chromatography. Using a mixture of hexane and benzene (10:90) as the eluting solvent, fractions 20 ml in volume (flow rate, 5 ml per min) were collected.

The contents of fractions 10 through 23 were pooled and the residue obtained upon evaporation of the solvent was recrystallized from acetone at −40° C. to give bis-3β,15α-hexadecanoyloxy-14α-ethyl-5α-cholest-7-ene (1.15 g; 12% yield) having the formula:

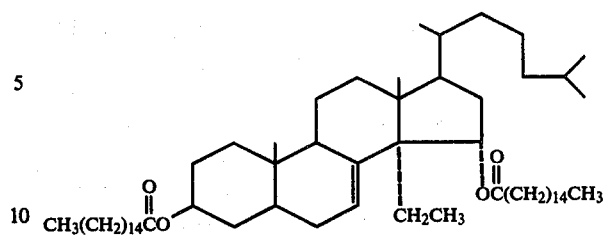

The contents of fractions 52 through 86 from the silica gel column were pooled and the residue obtained upon evaporation of the solvent was recrystallized from acetone at −40° C. to give 3β-hexadecanoyloxy-14α-ethyl-5α-cholest-7-en-15β-ol (1.62 g; 24% yield) having the formula:

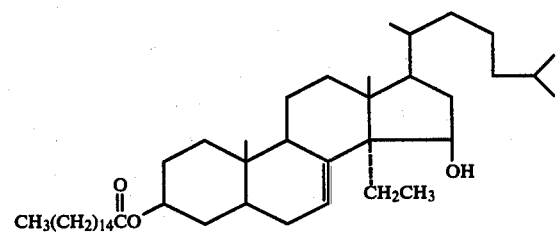

The contents of fractions 117 through 135 from the silica gel column were pooled and the residue obtained upon evaporation of the solvent was recrystallized from acetone at −40° C. to give 3β-hexadecanoyloxy-14α-ethyl-5α-cholest-7-en-15α-ol (2.35 g; 34% yield) having the formula:

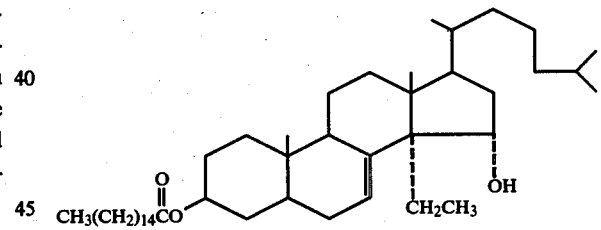

The structures of all three compounds were confirmed by i.r., n.m.r., and m.s. analyses. All three compounds showed a single component on thin-layer chromatographic analyses on silica gel G plates using a variety of solvent systems.

EXAMPLE 19

Preparation of 3β-Hexadecanoyloxy-14α-ethyl-5α-cholest-7-en-15-one

A solution of pyridinium chlorochromate (581 mg; 2.69 mmol) in dry methylene chloride (5 ml) was added in one portion to a solution of 3β-hexadecanoyloxy-14α-ethyl-5α-cholest-7-en-15β-ol (300 mg; 0.45 mmol). After stirring at room temperature (24° C.) for 30 min under nitrogen the mixture was poured into ether (400 ml) and washed successively with water, cold 0.6 N HCl, 0.47 M Na2CO3, and water. The resulting ether solution was dried over anhydrous magnesium sulfate and evaporated to dryness under reduced pressure to give a light yellow residue (284 mg). Analysis by thin-layer chromatography on a silica gel G plate (solvent, benzene) indicated one major component (~95%) with an $R_f$ of 0.50.

The material was subjected to medium pressure (100 p.s.i.) silica gel (0.032–0.063 min; 388 g) column (118 cm×1.5 cm) chromatography. Using benzene as the eluting solvent (flow rate, 5 ml per min), fractions 20 ml in volume were collected. The contents of fractions 12 through 35 were pooled and the residue obtained upon evaporation of the solvent was recrystallized from acetone-water to give 3β-hexadecanoyloxy-14α-ethyl-5α-cholest-7-en-15-one (207 mg; 89% yield) having the formula:

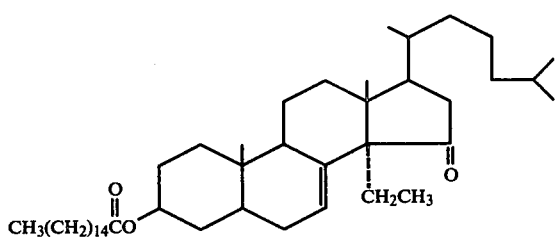

The structure was confirmed by i.r., n.m.r., and m.s. analyses. The compound showed a single component on thin-layer chromatographic analyses on silica gel G plates (solvent systems: benzene, 10% hexane in toluene, 10% ether in hexane, and petroleum ether-ether-acetic acid).

Treatment of 3β-hexadecanoyloxy-14α-ethyl-5α-cholest-7-en-15α-ol with pyridinium chlorochromate under the identical conditions described above gave 3β-hexadecanoyloxy-14α-ethyl-5α-cholest-7-en-15-one with the same melting point, infrared spectrum, nuclear magnetic resonance spectrum, mass spectrum, and thin-layer chromatographic behavior as described above for the 15-ketone derived from the 15β-hydroxy compound.

EXAMPLE 20

Preparation of
3β-Ethoxy-14α-ethyl-5α-cholest-7-en-15-ol

To 3β-ethoxy-14α-ethyl-5α-cholest-7-en-15-one (1.0 g; 2.19 mmol) in ether (100 ml) was added lithium aluminum hydride (2.0 g; 52.7 mmol). After stirring for 2 hours at room temperature, the reaction mixture was cooled to 0° C. and ice was cautiously added to decompose the unreacted hydride. The resulting mixture was poured into a 0.35 M NaCl solution and extracted thoroughly with ether containing methylene chloride (5%). The combined extracts were dried over anhydrous magnesium sulfate and evaporated to dryness under reduced pressure. The resulting residue (0.97 g) was crystallized from acetone-water to give a mixture (0.94 g; 94% yield) of 3β-ethoxy-14α-ethyl-5α-cholest-7-en-15β-ol and 3β-ethoxy-14α-ethyl-5α-cholest-7-en-15α-ol. The following structures for the compounds were shown by i.r., n.m.r., and m.s. analyses:

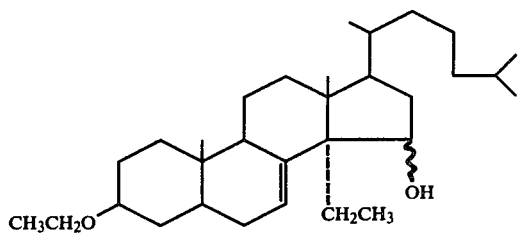

Analyses by thin-layer chromatography on silica gel G plates using five different solvent systems and by gas-liquid chromatography on 3% OV-1 and 3% OV-17 columns (column temperature, 270° C.) showed only one component. However, analysis of the trimethylsilyl ether derivative by gas-liquid chromatography on 3% OV-1 and 3% OV-17 columns (column temperature, 250° C.) indicated the presence of two components.

EXAMPLE 21

Preparation of
3β-Hexadecanoyloxy-5α-cholest-8(14)-en-15-one

Hexadecanoyl chloride (2.2 g; 8.0 mmol) was added to a solution of 5α-cholest-8(14)-en-3β-ol-15-one (2.0 g; 5.0 mmol) in dry pyridine (10 ml) and the resulting mixture was heated under reflux for one hour under an atmosphere of nitrogen. After cooling to room temperature, the reaction mixture was poured into water and thoroughly extracted with ether containing methylene chloride (5%). The combined ether extracts were washed successively with water, cold aqueous 5% hydrochloric acid, aqueous 5% sodium carbonate, and water and dried over anhydrous magnesium sulfate.

The residue obtained upon evaporation of the solvent was subjected to silica gel column chromatography (140 g; 60–200 mesh; 140 cm×2 cm). Using benzene as the eluting solvent, fractions 24 ml in volume (flow rate, 1.5 ml per min) were collected. The contents of fractions 9 through 40 were pooled and, after evaporation of the solvent under reduced pressure, recrystallized from acetone-water and acetone to give 3β-hexadecanoyloxy-5α-cholest-8(14)-en-15-one (3.80 g; 59.5% yield) having the formula:

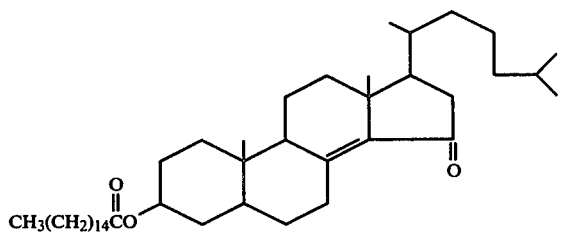

The structure of the compound was confirmed by i.r., n.m.r., and m.s. analyses. The compound showed a single component on thin-layer chromatographic analyses on silica gel G plates in three different solvent systems (benzene, 10% ether in benzene, and petroleum ether-hexane-acetic acid).

EXAMPLE 22

Preparation of 3β-Hemisuccinoyloxy-5α-cholest-8(14)-en-15-one

Succinic anhydride (2.5 g; 24.9 mmol) was added to a solution of 5α-cholest-8(14)-en-3β-ol-15-one (2.0 g; 5.0 mmol) in dry pyridine (20 ml) and the resulting mixture was heated under reflux for 5 hours under an atmosphere of nitrogen. After cooling to room temperature, the reaction mixture was poured into 0.034 N sodium chloride and ether (250 ml) containing methylene chloride (5%) was added. The separated ether phase was washed successively with cold aqueous 5% hydrochloric acid and water and dried over anhydrous magnesium sulfate.

The residue obtained upon evaporation of the solvent was recrystallized three times from acetone-water. The resulting crystals were treated with Norite A in acetone for 20 min, filtered through Hyflo Super-Cel, and crystallized by reducing the temperature to −78° C. The resulting crystalline product (1.8 g; 73% yield) was shown by i.r., n.m.r., and m.s. analyses to be 3β-hemisuccinoyloxy-5α-cholest-8(14)-en-15-one having the formula:

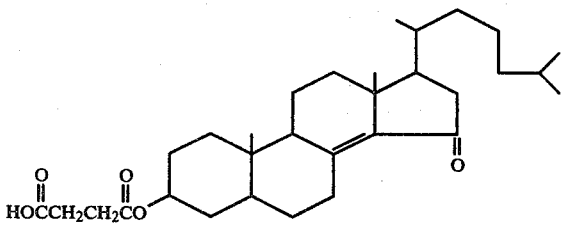

The compound showed a single component on thin-layer chromatographic analyses on silica gel G plates using either methanol or ethanol as developing solvents.

EXAMPLE 23

Preparation of 5α,14β-Cholest-7-en-15β-ol-3-one

To component 1 (200 ml) of the Bio-Dynamics (BMC Division) Cholesterol Auto Test was added "cholesterol oxidase" (6.0 ml; component 3 of the Cholesterol Auto Test) and the resulting mixture was diluted with distilled water (600 ml). 5α,14β-Cholest-7-en-3β,15β-diol (126 mg; 0.315 mmol) in isopropanol (35 ml) was added and the resulting mixture ws incubated with shaking at 37° C. for 7 hours. The mixture was extracted 4 times with 100 ml portions of chloroform. The extracts were combined, dried over anhydrous magnesium sulfate, and the volume was reduced to about 6 ml under reduced pressure.

The resulting material was subjected to preparative thin-layer chromatography on six silica gel G plates (750 microns in thickness) using ether as the developing solvent. The desired product was eluted from the plates with chloroform and, after evaporation of the solvent under reduced pressure, crystallized from acetone-water to give 83.2 mg (66% yield) of 5α,14β-cholest-7-en-15β-ol-3-one as needles melting at 90.5°–91.5° C. By i.r., n.m.r., and m.s. analyses, the structure of the product was established as:

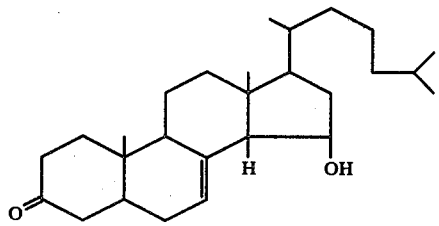

The compound showed a single component on thin-layer chromatographic analysis on a silica gel G plate (solvent:ether). Gas-liquid chromatographic analysis of the trimethylsilyl ether derivative on a 3% OV-17 column (column temperature, 250° C.) indicated the purity to be at least 98.9%.

EXAMPLE 24

Preparation of 5α,14β-Cholest-7-en-15α-ol-3-one

To component 1 (180 ml) of the Bio-Dynamics (BMC Division) Cholesterol Auto Test was added "cholesterol oxidase" (5.5 ml; component 3 of the Cholesterol Auto Test) and the resulting mixture was diluted with distilled water (540 ml). 5α,14β-Cholest-7-en-3β,15α-diol (105 mg; 0.262 mmol) in isopropanol (35 ml) was added and the resulting mixture was incubated with shaking at 37° C. After 5 hours of incubation, the solution turned cloudy. Additional isopropanol (10 ml) was slowly added and the incubation was continued for an additional 2.25 hours. The mixture was extracted 4 times with chloroform (100 ml portions) and the extracts were pooled, dried over anhydrous magnesium sulfate, and concentrated to a volume of about 4 ml.

The resulting material was subjected to preparative thin-layer chromatography on six silica gel G plates (750 microns in thickness) using ether as the developing solvent. The desired product was eluted from the plates with chloroform and, after evaporation of the solvent under reduced pressure, crystallized from acetone-water to give 75.3 mg (72% yield) of 5α,14β-cholest-7-en-15α-ol-3-one as fine needles melting at 121°–122° C. By i.r., n.m.r., and m.s. analyses, the structure of the product was confirmed as:

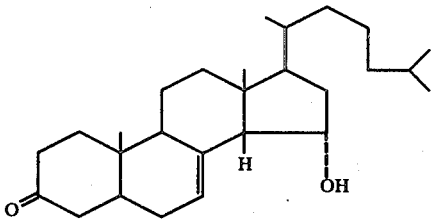

The compound showed a single component on thin-layer chromatographic analysis on a silica gel G plate (solvent:ether). Gas-liquid chromatographic analysis of the trimethylsilyl ether derivative on a 3% OV-17 column (column temperature, 250° C.) indicated the purity to be at least 98.6%.

EXAMPLE 25

Preparation of 14α-Ethyl-5α-cholest-7-en-15α-ol-3-one

To component 1 (250 ml) of the Bio-Dynamics (BMC Division) Cholesterol Auto Test was added "cholesterol oxidase" (16 ml; component 3 of the Cholesterol Auto Test) and the resulting mixture was diluted with distilled water (734 ml). 14α-Ethyl-5α-cholest-7-en-3β,15α-diol (100 mg) in isopropanol (20 ml) was added and the resulting mixture was incubated with shaking at 37° C. for 4.5 hours. The mixture was extracted 2 times with 100 ml portions of chloroform and the volume of the combined extracts was reduced to about 6 ml under reduced pressure.

This material was subjected to preparative thin-layer chromatography on silica gel G plates (750 microns in thickness) using ether as the developing solvent. The desired product was eluted from the plates with ether, and after evaporation of the solvent under reduced pressure, crystallized twice from ether-methanol to give 85.3 mg (85% yield) of 14α-ethyl-5α-cholest-7-en-15α-ol-3-one melting at 114°-115° C.

The compound showed a single component on gas-liquid chromatographic analysis on a 3% OV-17 column (column temperature, 270° C.). By i.r., n.m.r., and m.s. analyses, the structure of the product was confirmed as:

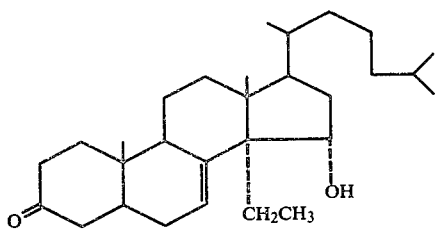

EXAMPLE 26

Preparation of 3β-Acetoxy-14α-n-butyl-5α-cholest-7-en-15-one

5α-Cholest-8(14)-en-3β-ol-15-one (10.0 g; 24.9 mmol) was added to a stirred solution of potassium t-butoxide, prepared by dissolving potassium metal (20.0 g) in t-butyl alcohol (1000 ml). n-Butyl iodide (300 ml) added in one portion to the reaction mixture and stirring was continued for 12 hours at room temperature. Water (400 ml) was added and the resulting mixture was extracted twice with 1000 ml portions of ether. The combined extracts were washed with water (200 ml), dried over anhydrous magnesium sulfate, and evaporated to dryness under reduced pressure to give a yellowish residue.

This residue was treated with acetic anhydride and pyridine and subjected to medium pressure (60 p.s.i.) silica gel (0.032-0.063 mm) column chromatography using 10% ether in benzene as the eluting solvent. After crystallization from acetone-water and repeated (3) medium pressure liquid column chromatographic purifications, 900 mg of a product was obtained. Upon crystallization from acetone-water, 850 mg of 3β-acetoxy-14α-n-butyl-5α-cholest-7-en-15-one, in the form of white needles, was recovered.

The compound showed a single component on thin-layer chromatographic analyses on silica gel G plates in eight different solvent systems (ether, 35% ethyl acetate in chloroform, 20% ether in chloroform, 20% ether in benzene, 10% ether in benzene, chloroform, benzene, and 10% hexane in benzene) and on gas-liquid chromatographic analyses on 3% OV-1 and 3% OV-17 columns (column temperature, 280° C.). By i.r., n.m.r., and m.s. analyses, the structure was confirmed as:

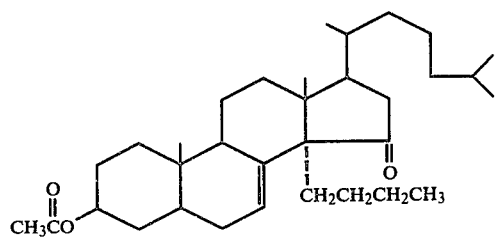

EXAMPLE 27

Preparation of 14α-n-Butyl-5α-cholest-7-en-3β-ol-15-one

A mixture of 3β-acetoxy-14α-n-butyl-5α-cholest-7-en-15-one (150 mg), 93% ethanol (53 ml), and KOH (1.05 g) was heated under reflux for 1.5 hours. After reduction of the volume to about ½ of its initial value, the mixture was poured into a 0.86 N sodium chloride solution (200 ml) and the resulting mixture was thoroughly extracted with ether containing methylene chloride (5%). The combined extracts were washed with water, dried over anhydrous magnesium sulfate, and evaporated to dryness under reduced pressure. The residue (130 mg) so obtained was crystallized from acetone-water to give 120 mg (87% yield) of fine needles of 14α-n-butyl-5α-cholest-7-en-3β-ol-15-one, having the structure:

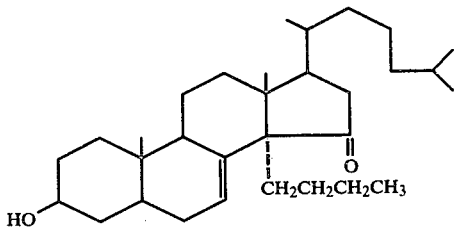

The structural formula was confirmed by i.r., n.m.r., and m.s. analyses. The compound showed a single component on thin-layer chromatographic analyses on silica gel G plates in eight different solvent systems (ether, 35% ethyl acetate in chloroform, 20% ether in chloroform, 20% ether in benzene, 10% ether in benzene, chloroform, benzene, and 10% hexane in benzene). The purity was in excess of 99% as judged by gas-liquid chromatographic analyses of the trimethylsilyl ether derivative on 3% OV-1 and 3% OV-17 columns (column temperature, 270° C.).

EXAMPLE 28

Preparation of Bis-3β,15α-acetoxy-14α-n-butyl-5α-cholest-7-ene and 3β-acetoxy-14α-n-butyl-5α-cholest-7-en-15β-ol To 3β-acetoxy-14α-n-butyl-5α-cholest-7-en-15-one (647 mg; 1.3 mmol) in ether (30 ml) was added lithium aluminum hydride (1.2 g; 32 mmol). After 3 hours the reaction mixture was cooled to 0° C. and ethyl acetate was cautiously added to decompose the unreacted hydride. The resulting mixture was poured into a 0.86 N sodium chloride solution (200 ml) and extracted twice with ether containing methylene chloride (5%).

The combined extracts were dried over anhydrous magnesium sulfate and evaporated to dryness under reduced pressure to give a white residue (570 mg). This material showed two components on thin-layer chromatographic analysis on a silica gel G plate (solvent system: 10% ether in benzene).

The white residue (570 mg) was dissolved in dry pyridine (10 ml) and acetic anhydride (10 ml) was added. After standing for 15 hours at room temperature the reaction mixture was poured into ice and the resulting mixture was extracted twice with 200 ml portions of ether containing methylene chloride (5%). The combined extracts were washed successively with water, cold 1N HCl, aqueous 5% sodium carbonate, and water, dried over anhydrous magnesium sulfate, and evaporated to dryness under reduced pressure.

The residue (620 mg) so obtained was subjected to medium pressure liquid chromatography on a silica gel (0.032–0.063 mm) column using 1% ether in benzene as the eluting solvent. The contents of the fractions corresponding to the expected mobility of the diacetate were combined and, after evaporation of the solvent, crystallized from acetone-water to give needles of bis-3β,15α-acetoxy-14α-n-butyl-5α-cholest-7-ene. By i.r., n.m.r., and m.s. analyses, the structure was confirmed as:

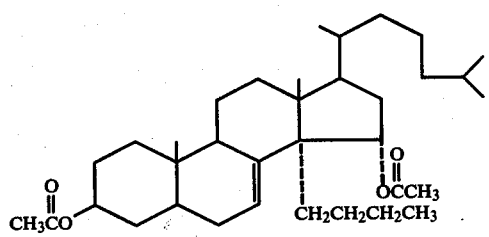

The compound showed a single component on thin-layer chromatographic analyses on silica gel G plates in eight different solvents systems (ether, 35% ethyl acetate in chloroform, 20% ether in chloroform, 20% ether in benzene, 10% ether in benzene, chloroform, benzene, and 10% hexane in benzene).

The contents of the fractions with the expected mobility of the monoacetate were combined and, after evaporation of the solvent under reduced pressure, crystallized from acetone-water to give fine needles of 3β-acetoxy-14α-n-butyl-5α-cholest-7-en-15β-ol (190 mg).

The compound showed a single component on a thin layer chromatographic analyses on silica gel G plates in eight different solvent systems (ether, 35% ethyl acetate in chloroform, 20% ether in chloroform, 20% ether in benzene, 10% ether in benzene, chloroform, benzene, and 10% hexane in benzene) and a purity in excess of 99% on gas-liquid chromatographic analysis of the trimethylsilyl ether derivative on a 3% OV-17 column. The structure was confirmed by i.r., n.m.r., and m.s. analyses to be:

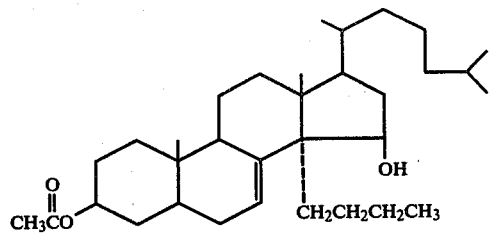

EXAMPLE 29

Preparation of 14α-n-Butyl-5α-cholest-7-en-3β,15α-diol

To bis-3β,15α-acetoxy-14α-n-butyl-5α-cholest-7-ene (200 mg; 0.37 mmol) in ether (30 ml) was added lithium aluminum hydride (400 mg; 10.5 mmol). After 2 hours at room temperature, the reaction mixture was cooled to 0° C. and ethyl acetate was cautiously added to decompose the unreacted hydride. The mixture was poured into a 0.86 N sodium chloride solution and extracted twice with ether containing methylene chloride (5%). The combined extracts were dried over anhydrous magnesium sulfate and evaporated to dryness under reduced pressure.

The residue (180 mg) was subjected to medium pressure liquid chromatography on a silica gel (0.032–0.063 mm) column using 15% ether in benzene as the eluting solvent. The contents of the fractions corresponding to the mobility of the desired diol were pooled and, after evaporation of the solvent under reduced pressure, crystallized from acetone-water to give needles of 14α-n-butyl-5α-cholest-7-en-3β,15α-diol (128 mg) having the structural formula:

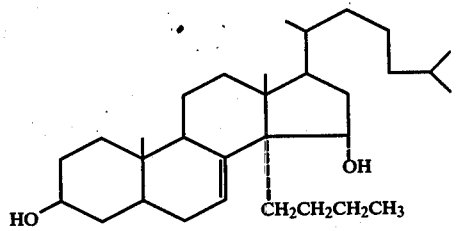

The structure was confirmed by i.r., n.m.r., and m.s. analyses. The compound showed a single component on thin-layer chromatographic analyses on silca gel G plates in eight different solvent systems and showed a purity in excess of 99% on gas-liquid chromatographic analysis of the trimethylsilyl ether derivative on a 3% OV-17 column (column temperature, 270° C.).

EXAMPLE 30

Preparation of 14α-n-Butyl-5α-cholest-7-en-3β,15β-diol

To 3β-acetoxy-14α-n-butyl-5α-cholest-7-en-15β-ol (100 mg; 0.20 mmol) in ether (30 ml) was added lithium aluminum hydride (200 mg; 5.26 mmol). After 2 hours at room temperature the reaction mixture was cooled to 0° C. and ethyl acetate was cautiously added to decompose the excess hydride. The mixture was poured into a 0.86 N sodium chloride solution and extracted twice with ether containing methylene chloride (5%). The combined extracts were dried over anhydrous magnesium sulfate and evaporated to dryness under reduced pressure.

The glassy residue (180 mg) was subjected to medium pressure liquid chromatography on a silica gel (0.032–0.063 mm) column using 15% ether in benzene as the eluting solvent. The contents of the fractions corresponding to the mobility of the desired diol were pooled and, after evaporation of the solvent, gave 14α-n-butyl-5α-cholest-7-en-3β,15β-diol (80 mg) as a white amorphous solid which could not be obtained in crystalline form from acetone-water or methanol-water.

The compound showed a single component on thin-layer chromatographic analyses on silica gel G plates in eight different solvent systems and had a purity of at least 98.5% as judged by gas-liquid chromatographic analysis of the trimethylsilyl ether derivative on a 3% OV-17 column (column temperature, 270° C.). The structure was confirmed by i.r., n.m.r., and m.s. analyses to be:

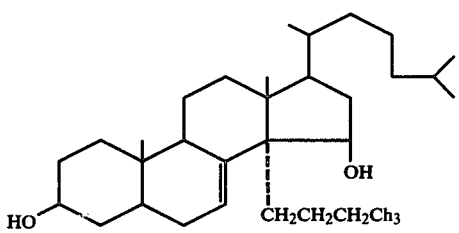

EXAMPLE 31

Preparation of 3α-Benzoyloxy-5α-cholest-8(14)-en-15-one

A solution of diethyl azodicarboxylate (0.87 g; 5.0 mmol) in tetrahydrofuran (5 ml) was added dropwise to a stirred solution of 5α-cholest-8(14)-en-3β-ol-15-one (1.00 g; 2.5 mmol), triphenyl phosphine (1.97 g; 7.5 mmol), and benzoic acid (0.61 g; 5.0 mmol) in dry tetrahydrofuran (30 ml). After stirring for 14 hours, the mixture was poured into water and thoroughly extracted with ether containing methylene chloride (5%). The combined extracts were dried over anhydrous magnesium sulfate and evaporated to dryness under reduced pressure.

The resulting light yellow solid was subjected to silica gel (100 g; 60–300 mesh) column (60 cm×2.0 cm) chromatography. Using benzene as the eluting solvent, fractions 24 ml in volume (flow rate, 1.5 ml per min) were collected. The contents of fractions 40 through 95 were pooled and, after evaporation of the solvent under reduced pressure, crystallized from acetone-water to give crystalline 3α-benzoyloxy-5α-cholest-8(14)-en-15-one. By i.r., n.m.r., and m.s. analyses, the structure was confirmed as:

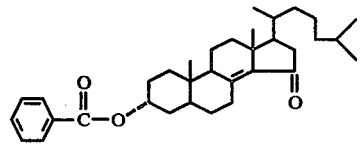

The compound showed a single component on thin-layer chromatographic analyses on silica gel G plates (solvent systems: benzene, 10% ether in benzene, 10% ether in hexane, 5% acetone in chloroform, and 35% ethyl acetate in chloroform).

EXAMPLE 32

Preparation of 5α-Cholest-8(14)-en-3α-ol-15-one

To 3α-benzoyloxy-5α-cholest-8(14)-en-15-one (500 mg; 1.00 mmol) in absolute ethanol (175 ml) was added water (10 ml) and concentrated sulfuric acid (30 ml). After heating the mixture under reflux for 24 hours in an atmosphere of nitrogen, the volume was reduced to about ⅓ of its initial value under reduced pressure and poured into water. The mixture was thoroughly extracted with ether containing methylene chloride (5%) and the combined extracts were evaporated to dryness under reduced pressure.

The resulting light yellow residue was crystallized twice from acetone-water. The crystals were dissolved in acetone and warmed in the presence of decolorizing carbon (Norite A) for 15 min. The solution was filtered through Hyflo Super-Cel (Johns-Manville Corp.) and the Super-Cel was washed with methanol. The acetone and methanol solutions were combined and, after the addition of water, a crystalline product (326 mg; 82% yield) formed and was collected and dried in vacuo. Analyses by i.r., n.m.r., and m.s. confirmed the product as 5α-cholest-8(14)-en-3α-ol-15-one having the structural formula:

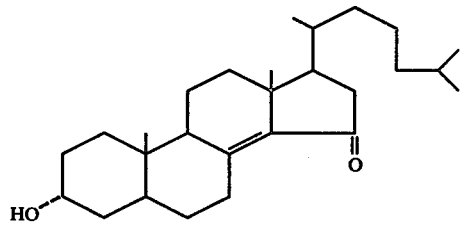

The compound showed a single component on thin-layer chromatographic analyses on silica gel G plates (solvent systems: 10% ether in benzene, 5% acetone in chloroform, and 35% ethyl acetate in chloroform) and on gas-liquid chromatographic analyses on 3% OV-1 and 3% OV-17 columns (column temperature, 270° C.).

EXAMPLE 33

Preparation of 3α-Benzoyloxy-14α-ethyl-5α-cholest-7-en-15-one

A solution of diethyl azodicarboxylate (1.74 g; 10.0 mmol) in tetrahydrofuran (10 ml) was added dropwise to a stirred solution of 14α-ethyl-5α-cholest-7-en-3β-ol-15-one (2.14 g; 5.0 mmol), triphenyl phosphine (3.93 g; 15.0 mmol), and benzoic acid (1.22 g; 10.0 mmol) in dry tetrahydrofuran (60 ml). After stirring for 14 hours, the mixture was poured into water and thoroughly extracted with ether containing methylene chloride (5%). The combined extracts were dried over anhydrous magnesium sulfate and evaporated to dryness under reduced pressure.

The resulting light yellow solid was subjected to medium pressure (100 p.s.i.) liquid chromatography on a silica gel (388 g; 0.032–0.063 mm) column (118 cm×1.5 cm). Using benzene as the eluting solvent, fractions 20 ml in volume (flow rate, 1.5 ml per min) were collected. The contents of fractions 13 through 50 were pooled and, after evaporation of the solvent under reduced pressure, crystallized from acetone-water to give crystalline 3α-benzoyloxy-14α-ethyl-5α-cholest-7-en-15-one (2.45 g; 92% yield).

The compound showed a single component on thin-layer chromatographic analyses on silica gel G plates (solvent systems: benzene, 10% ether in benzene, and 10% ether in hexane). The structure, by i.r., n.m.r., and m.s. analyses, was confirmed to be:

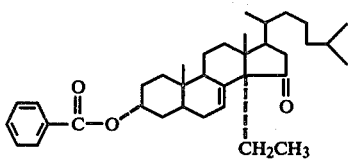

EXAMPLE 34

Preparation of 14α-Ethyl-5α-cholest-7-en-3α-ol-15-one

To 3α-benzoyloxy-14α-ethyl-5α-cholest-7-en-15-one (1.0 g; 1.9 mmol) in absolute ethanol (190 ml) was added a solution of KOH (4.0 g) in water (10 ml). After heating under reflux in an atmosphere of nitrogen for 2 hours, the volume of the mixture was reduced to about 100 ml under reduced pressure. The mixture was poured into water and thoroughly extracted with ether containing methylene chloride (5%). The combined extracts were dried over anhydrous magnesium sulfate and evaporated to dryness under reduced pressure. The resulting white residue was crystallized from acetone-water to give 14α-ethyl-5α-cholest-7-en-3α-ol-15-one (0.72 g; 89% yield).

The compound showed a single component on thin-layer chromatographic analyses on silica gel G plates (solvent systems: 10% ether in benzene, 5% acetone in chloroform, and 35% ethyl acetate in chloroform), and on gas-liquid chromatographic analyses on 3% OV-1 and 3% OV-17 columns (column temperature, 270° C.). The structure, by i.r., n.m.r., and m.s. analyses, was confirmed to be:

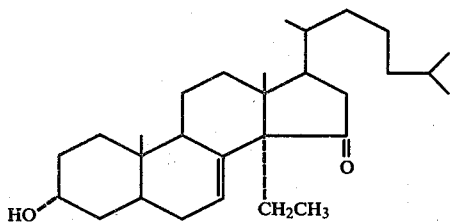

EXAMPLE 35

Preparation of 5α-Cholest-8(14)-en-15α-ol-3-one

To component 1 (180 ml) of Biodynamics (BMC Division) Cholesterol Auto Test was added "cholesterol oxidase" (5.5 ml; component 3 of the Cholesterol Auto Test) and the resulting mixture was diluted with distilled water (540 ml). 5α-Cholest-8(14)-en-3β,15α-diol (105 mg; 0.26 mmol) in isopropanol (40 ml) was added and the resulting mixture was incubated with shaking for 8 hours at 37° C.

A saturated solution (200 ml) of sodium chloride was added and the mixture was extracted 5 times with 100 ml portions of chloroform. The combined organic extracts were dried over anhydrous magnesium sulfate and evaporated to dryness under reduced pressure.

The resulting residue was subjected to silica gel (150 g; 70-325 mesh) column (90 cm×2.0 cm) chromatography using 10% ether in benzene as the eluting solvent (flow rate, 5 ml per min). Fractions 20 ml in volume were collected. The contents of fractions 25 through 45 were pooled and, after evaporation of the solvent under reduced pressure, crystallized from acetone-water to give 5α-cholest-8(14)-en-15α-ol-3-one (88 mg; 85% yield) having the formula:

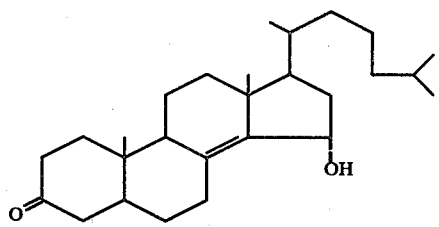

The structure of the compound was confirmed by i.r., n.m.r., and m.s. analyses. The compound showed a single component on thin-layer chromatographic analyses on silica gel G plates (solvent system: 10% ether in benzene, 35% ethyl acetate in chloroform, and 5% acetone in chloroform) and a purity in excess of 98% on gas-liquid chromatographic analyses on 3% OV-1 and 3% OV-17 columns (column temperature, 270° C.).

EXAMPLE 36

Preparation of 5α-Cholest-8(14)-en-15-one-3β-yl pyridinium sulfate

Pyridine-sulfur trioxide (5.0 g) was added to 5α-cholest-8(14)-en-3β-ol-15-one (2.0 g; 5.0 mmol) in dry chloroform (50 ml; ethanol-free; dried over Linde molecular sieve, type 3A). The resulting mixture was stirred at room temperature for 3 hours. The excess reagent was removed by filtration, washed with a small volume of chloroform, and the filtrate was cooled to −40° C. in a dry ice-acetone bath and filtered through Hyflo Super-Cel (Johns-Manville Corp.). Hexane was added to the chloroform filtrate until a cloudiness appeared whereupon cooling to 0° C. gave a white precipitate. This material was collected by filtration and placed in a vacuum desiccator for 100 hours at room temperature to remove all traces of solvent. The product, 5α-cholest-8(14)-en-15-one-3β-yl pyridinium sulfate (2.4 g; 86% yield), had the following structural formula as confirmed by i.r., n.m.r., and m.s. analyses:

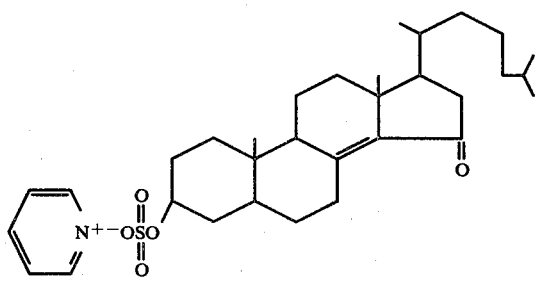

The product showed a single component on thin-layer chromatographic analyses on silica gel G plates (solvent systems: 25% ethyl acetate in methanol and 25% ethyl acetate in ethanol).

EXAMPLE 37

Preparation of 5α-Cholest-8(14)-en-15-on-3β-yl potassium sulfate (monohydrate)

5α-Cholest-8(14)-en-15-on-3β-yl pyridinium sulfate (1.0 g; 1.79 mmol) was dissolved in distilled water (50 ml) at room temperature and an aqueous saturated solution of potassium chloride was slowly added to the stirred mixture. After 15 min the resulting suspension was filtered, washed with water, and dried in a vacuum desiccator for several hours. The resulting white residue (0.85 g; 89%), was shown by i.r., n.m.r., and m.s. analyses to be 5α-cholest-8(14)-en-15-on-3β-yl potassium sulfate (monohydrate) having the structure:

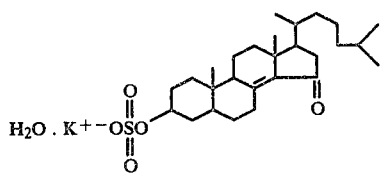

EXAMPLE 38

Preparation of 5α-cholest-8(14)-3,15-dione

To a dry methylene chloride solution of 5α-cholest-8(14)-en-3β,15α-diol (0.4 g, 1.0 mmol in 20 ml) was added a solution of chromium trioxide (3 g) in a mixture of dry methylene chloride (40 ml) and dry pyridine (3 ml). The reaction mixture was stirred for 15 min under nitrogen, ether was added, and the solution washed with cold 5% hydrochloric acid and water. The solution was dried with magnesium sulfate, filtered, and evaporated at reduced pressure to yield a residue (0.35 g) which was purified by preparative thin-layer chromatography (silicic acid; solvent:benzene). The product was recrystallized from acetone-water (yield: 0.332 g, 84%) and was shown by i.r., n.m.r., and m.s. analyses to be 5α-cholest-8(14)-3,15-dione having the formula:

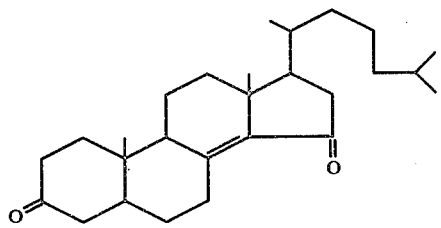

EXAMPLE 39

Preparation of 14α-Ethyl-5α-cholest-7-en-15-oxo-3β-yl Potassium Sulfate (Monohydrate)

To a stirred solution at room temperature of 14α-Ethyl-5α-cholest-7-en-15-on-3β-yl pyridinium sulfate (500 mg; 0.85 mmol) in distilled water (25 ml), a saturated aqueous solution of potassium chloride (15 ml) was slowly added. After 10 min the stirred suspension was filtered, washed with distilled water, and dried in a vacuum desiccator for several hours. The white residue (418 mg, 87%) was shown by i.r., n.m.r., and m.s. analyses to be 14α-ethyl-5α-cholest-7-en-15-on-3β-yl potassium sulfate (monohydrate) having the formula:

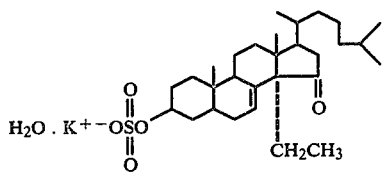

EXAMPLE 40

Preparation of 14α-Ethyl-5α-cholest-7-en-15-on-3β-yl pyridinium sulfate

14α-Ethyl-5α-cholest-7-en-3β-ol-15-one (1.0 g; 2.33 mmol) was dissolved in dry chloroform (25 ml; ethanol-free; dried over Linde molecular sieve, type 3A). Pyridine-sulfur trioxide (2.5 g) was added and the mixture stirred at room temperature for 3 hours. The excess reagent was removed by filtration and washed with a small volume of chloroform. The filtrate was cooled to −40° C. in a dry ice-acetone bath and filtered through Hyflo Super-Cel (Johns-Manville Corp.). Hexane was added to the chloroform filtrate until a cloudiness appeared. Upon cooling to 0° C., a white precipitate formed which was collected by filtration and placed in a vacuum desiccator for 100 hours at room temperature to remove all traces of solvent. The product (1.2 g; 88% yield) was shown by i.r., n.m.r., and m.s. analyses to be 14α-ethyl-5α-cholest7-en-15-on-3β-yl pyridinium sulfate having the structure:

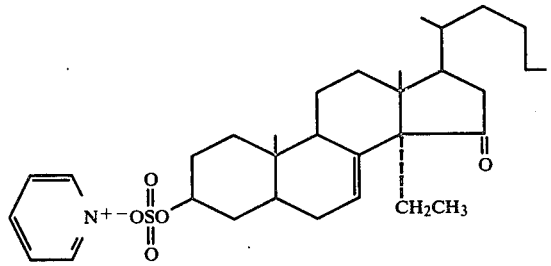

The compound showed a single component on thin-layer chromatographic analyses on silica gel G plates (solvent systems: 25% ethyl acetate in methanol and 25% ethyl acetate in ethanol).

EXAMPLE 41

Effect of 3β-Hexadecanoyloxy-5α-cholest-8(14)-en-15-one and 3β-hemisuccinoyloxy-5α-cholest-8(14)-en-15-one on Serum Cholesterol Levels in Rats Male rats of the Sprague-Dawley strain were fed Purina rat chow ad libidum. The rats were maintained on a light (7 A.M.–6 P.M.) -dark (6 P.M.–7 A.M.) cycle throughout the study and for a period of at least 4 days prior to the initiation of the study.

3β-Hexadecanoyloxy-5α-cholest-8(14)-en-15-one (5 mg; dissolved in 0.25 ml of triolein), hereafter referred to as the "palmitate ester", or 3β-hemisuccinoyloxy-5α-cholest-8(14)-en-15-one (5 mg; suspended in 0.25 ml of triolein through the use of a tight-fitting all-glass homogenizer), hereafter referred to as the "hemisuccinate ester", were administered subcutaneously once a day at about 12 P.M. to each of eight and six rats, respectively. Control animals (8) received daily injections of triolein (0.25 ml).

The control animals had an initial mean body weight of 163.5 g [±5.6, standard error of mean (S.E.M.)]. The rats receiving the palmitate and hemisuccinate esters had initial mean values for body weight of 178.5 g (±5.5, S.E.M.) and 170.0 g (±4.7, S.E.M.), respectively.

Blood samples were taken from the rats periodically and the serum cholesterol concentrations measured, in duplicate, by the method of Abell et al., J. Biol. Chem., the palmitate, hemisuccinate, and triolein groups were (mean±S.E.M.) 40.5±4.6, 40.7±1.6, and 43.6±3.3, respectively.

There was no significant difference between the mean values of the liver weights of the triolein-treated rats (9.6 g±0.4, S.E.M.) and the hemisuccinate ester-treated rats (10.6 g±0.4, S.E.M.). Similarly, there was no significant difference between the mean values of the liver weights when expresses as a percentage of the total body weight, between the triolein-treated rats (;b 4.09%±0.08, S.E.M.) and the hemisuccinate ester-treated rats (4.36%±0.08, S.E.M.).

TABLE I

EFFECTS OF TRIOLEIN, 3β-HEXADECANOYLOXY-5α-CHOLEST-8(14)-EN-15-ONE (PALMITATE ESTER), AND 3β-HEMISUCCINOYLOXY-5α-CHOLEST-8-(14)-EN-15-ONE (HEMISUCCINATE ESTER) ON SERUM CHOLESTEROL LEVELS IN RATS

| | Serum Cholesterol - mg per 100 ml (Mean ± S.E.M.) | | | % Reduction (Mean ± S.E.M.) | |
|---|---|---|---|---|---|
| Day | Triolein | Palmitate Ester | Hemisuccinate Ester | Palmitate Ester | Hemisuccinate Ester |
| 0 | 82.6 ± 2.3 | 91.6 ± 2.6 | 89.1 ± 2.6 | — | — |
| 3 | 79.6 ± 2.5 | 74.9 ± 3.9 | 78.6 ± 2.4 | 18.2 ± 3.3 | 13.5 ± 4.4 |
| 6 | 76.4 ± 3.0 | 75.8 ± 5.0 | 72.5 ± 1.9 | 15.7 ± 4.4 | 18.1 ± 4.1 |
| 9 | 82.1 ± 2.0 | 77.9 ± 5.9 | 72.3 ± 1.6 | 14.5 ± 2.9 | 18.4 ± 3.5 |
| 12 | 79.4 ± 2.2 | 61.4 ± 3.9 | 58.8 ± 2.8 | 33.2 ± 2.7 | 33.9 ± 2.9 |

Vol. 195, pp. 357–366 (1966). The results are reported in Table I.

Due to the fact that the groups of rats were not matched with respect to serum cholesterol levels prior to the start of the experiment, the initial mean values of the serum cholesterol levels for the triolein, palmitate ester, and hemisuccinate ester groups were not identical. Despite this fact, the results presented in Table I clearly indicate significant decreases in serum cholesterol levels after 3, 6, 9, and 12 days of treatment with the palmitate ester and the hemisuccinate ester when compared with the mean value for the same rats prior to the initiation of administration of the compound. In contrast, the rats receiving daily injections of the triolein showed no significant change in serum cholesterol level. Moreover, the mean value of the serum cholesterol levels in the palmitate and hemisuccinate ester groups after 12 days of treatment was significantly lower than the corresponding mean value of the serum cholesterol levels of the triolein-treated rats.

The effects of the palmitate ester and the hemisuccinate ester on the serum cholesterol levels in the individual rats were also analyzed. Table I presents the mean values of the percentage reduction of the serum cholesterol levels from the initial levels in the same rats and also presents expressions of the variations in these values. Significant reduction in serum cholesterol levels was observed in each rat in both groups. The percentage reduction of the serum cholesterol level after 12 days of treatment with the palmitate ester ranged from 22.7% to 48.9%. The percentage reduction of the serum cholesterol level after 12 days of treatment with the hemisuccinate ester ranged from 28.5% to 46.3%.

Analysis of the serum sterols of the rats after 12 days of treatment with either the palmitate ester or the hemisuccinate ester by gas-liquid chromatography (3% OV-1 on Gas-Chrom Q) indicated no detectable accumulation (<1%) of sterols other than cholesterol.

There were no significant differences in the growth of the rats treated with 5 mg per day of either the palmitate or hemisuccinate esters when compared with the group receiving the triolein alone. The average percentage weight gain over the total experimental period in The mean values of the liver weights of the triolein-treated rats (9.6 g±0.08, S.E.M.). S.E. differed from those of the palmitate ester-treated rats (11.4 g±0.5, S.E.M.). Similarly, the mean value of the liver weights, when expressed as a percentage of the total body weight, of the triolein-treated rats (4.09%±0.08, S.E.M.) differed from the mean value for the palmitate ester-treated rats (4.53%±0.09, S.E.M.).

EXAMPLE 42

Following generally the procedure described in Example 41, 3β-Ethoxy-14α-ethyl-5α-cholest-7-en-15-one (5 mg) in triolein (0.25 ml) was administered subcutaneously once a day to each of eight rats. Control animals (8) received daily injections of triolein (0.25 ml). The control animals had an initial mean body weight of 143.7 g (±6.3, S.E.M.) and the rats receiving the steroidal ketone had an initial mean body weight of 141.8 g (±2.9, S.E.M.).

Similarly, 5α-cholest-8(14)-en-3β-ol-15-one (2mg) in (0.2 ml) olive oil or 5.0 mg in 0.5 ml of olive oil) was administered subcutaneously once a day to each of a group of rats. The 2 mg dose was administered to 12 rats, while a like number of rats received daily injections of 0.2 ml olive oil. 5 mg doses were administered to each of 6 rats, while 6 control animals received daily injections of 0.5 ml olive oil. The rats used in this study initially weighed between 110 and 190 grams.

The mean serum cholesterol values for the control and experimental animals are presented in Table II. Significant reductions in serum cholesterol levels (relative to the control rats) were observed in the rats receiving daily subcutaneous injections of 15-oxygenated sterols. The mean serum cholesterol levels in the olive oil and triolein-treated animals did not differ significantly during the period of the study. The average percentage reduction in serum cholesterol levels in the individual rats treated with the 14α-ethyl-15-ketone (day 27 vs. day 0) ranged from 12.1 to 34.9. The mean value was 25.0 (±2.3, S.E.M.).

There were no significant differences in the growth of the rats treated with the 15-oxygenated sterols and the rats treated with triolein or olive oil.

TABLE II

EFFECTS OF 3β-ETHOXY-14α-ETHYL-5α-CHOLEST-7-EN-15-ONE AND 5α-CHOLEST-8(14)-EN-3β-OL-15-ONE ON SERUM CHOLESTEROL LEVELS IN RATS

| | Serum Cholesterol mg per 100 ml (Mean ± S.E.M.) | | |
|---|---|---|---|
| Day | Triolein | 3β-Ethoxy-14α-ethyl-5α-cholest-7-en-15-one | % Reduction (relative to triolein-treated rats) |
| 0 | 88.9 ± 2.2 | 89.1 ± 2.2 | — |
| 3 | — | — | — |
| 6 | 81.2 ± 2.8 | 77.3 ± 2.1 | 4.8 |
| 10 | 82.9 ± 3.0 | 80.1 ± 2.3 | 3.4 |
| 15 | 81.6 ± 3.5 | 78.5 ± 3.3 | 3.8 |
| 21 | 82.6 ± 3.8 | 73.1 ± 2.3 | 11.5 |
| 27 | 81.8 ± 3.3* | 66.8 ± 2.6 | 18.3 |

| Day | Olive Oil (0.2 ml) | 5α-cholest-8(14)-en-3β-ol-15-one-(2 mg) | % Reduction (relative to olive oil-teated rats) |
|---|---|---|---|
| 3 | 73.7 ± 2.9 | 64.5 ± 2.5 | 12 |

| Day | Olive Oil (0.5 ml) | 5α-cholest-8(14)-en-5β-ol-15-one-(5 mg) | % Reduction (relative to olive oil-treated rats) |
|---|---|---|---|
| 3 | 79.5 ± 5.8 | 59.6 ± 2.2 | 22 |

*The values for this mean and S.E.M. were calculated after deleting one rat which had a very low serum cholesterol (55.3 mg per 100 ml) on this day. Inclusion of this value gave a mean serum cholesterol level of 78.5 ± 4.2 (S.E.M.).

EXAMPLE 43

Male rats of the Sprague-Dawley strain were purchased from Sprague-Dawley Farms (Madison, Wisconsin). The rats were maintained on a light (7:00 A.M.–5:30 P.M.)—dark (5:30 P.M.–7:00 A.M.) cycle and fed a Cholesterol Free Test Diet (United States Biochemical Corporation, Cleveland, Ohio) for a period of 13 days prior to the initiation of the experimental period. Six days prior to the initiation of the experimental period blood samples were taken for assay of serum cholesterol concentration and, based upon the results of these analyses, rats were divided into 3 groups with approximately the same mean serum cholesterol concentration. The rats were then individually housed in metabolic cages (Econo-Metabolism Units, Maryland Plastics, New York, New York) for 6 days prior to the initiation of the experimental period. The animals were maintained on the light-dark cycle throughout the experimental period.

The individual animals were weighed daily throughout the experimental period. Food consumption by the individual rats was similarly recorded daily. No significant spillage of the food or contamination of the food by feces or urine was possible due to the nature of the matabolic cage and the food receptacles utilized.

Blood samples were taken from the tail vein between 8:15 A.M. and 9:30 A.M. and at no time was more than ~0.5 ml of blood removed. Serum was obtained by centrifugation of the blood using Sure-Sep Junior (General Diagnostics, Division of Warner Lambert Company, Morris Plains, New Jersey) for 20 min at 2000–2500 rpm in a table top centrifuge (Dynac, Clay Adams Model 0091). Serum cholesterol concentration was assayed by a modification of the Cholesterol Auto Test (Bio-Dynamics, BMC Division) as described in Bio-Dynamics/bmc Cholesterol Instruction (revised December, 1975).

5α-Cholest-8(14)-en-3β-ol-15-one (500 mg), prepared and purified as described in Example 1, was added in small portions to 500 g of the Cholesterol Free Test Diet in a 2 liter glass stoppered bottle. After each addition of the sterol to the diet, the bottle was rolled and shaken thoroughly. The resulting 0.1% diet with respect to the 5α-cholest-8(14)-en-3β-ol-15-one was stored at 4° C. Prior to use in feeding, the diet was allowed to warm to room temperature (~25° C.).

The rats were divided into 3 groups hereafter designated as

1. Ad libidum group—6 rats with free access to the Cholesterol Free Test Diet.
2. Ketone group—7 rats with free access to the Cholesterol Free Test Diet containing 0.1% 5α-cholest-8(14)-en-3β-ol-15-one.
3. Pair-fed group—7 rats with access to the Cholesterol Free Test Diet but only in the amount consumed by its individual counterpart in the ketone group on the previous day.

At the initiation of the experimental period the mean serum cholesterol concentrations (mg per 100 ml of serum±standard error of mean) for the 3 groups were as follows:

Ad libidum—71.4±2.4
Ketone—71.2±0.9
Pair-fed—69.0±2.9

At the initiation of the experimental period the mean body weight values (±standard error of mean) were as follows:

Ad libidum—125.3±4.4
Ketone—130.4±4.4
Pair-fed—128.0±4.0

Thus, the groups were well-matched with respect to mean body weight and mean serum cholesterol concentration.

The 5α-cholest-8(14)-en-3β-ol-15-one administered in the diet as described above had a marked effect in lowering the serum cholesterol concentrations. The mean serum cholesterol level (mg per 100 ml of serum) of the rats receiving the 0.1% 5α-cholest-8(14)-en-3β-ol-15-one in the diet decreased from an initial value of 71.2 to a value of 50.1 on day 4 and to 36.9 on day 8 of the experimental period. The mean values of the serum cholesterol concentration in the ad libidum group and the pair-fed group did not change significantly during the experimental period. This data is presented in table III.

TABLE III

| SERUM CHOLESTEROL CONCENTRATION (mg per 100 ml) | | | |
|---|---|---|---|
| Day | 0 | 4 | 8 |
| Ad libidum | 71.4 ± 2.4 | 69.9 ± 2.7 | 70.5 ± 2.4 |
| Ketone | 71.2 ± 0.9 | 50.1 ± 2.3 | 36.9 ± 3.3 |
| Pair-fed | 69.0 ± 2.9 | 71.8 ± 4.2 | 74.9 ± 4.5 |

The data on the serum cholesterol levels for the 3 groups as a percentage of the value of the initial level (Day 0) in the individual rats after 4 and 8 days are presented in Table IV. There was no significant change in the serum cholesterol concentration in the ad libidum group or in the pair-fed group. However, of rats fed the ketone the mean value for the percentage of the serum cholesterol level on day 4 and day 8 of the period relative to the initial values were 70.5% and 51.8%, respectively.

TABLE IV

| SERUM CHOLESTEROL CONCENTRATION PERCENTAGE OF INITIAL LEVELS IN INDIVIDUAL RATS | | | |
|---|---|---|---|
| | Ad Libidum | Ketone | Pair-fed |
| Day 4 | 98.9 ± 6.3 | 70.5 ± 3.6 | 96.1 ± 8.1 |
| Day 8 | 99.0 ± 2.2 | 51.8 ± 4.4 | 109.1 ± 6.1 |

The average daily food consumption on days 2 through 7 of the rats in the three groups were as follows:
Ad libidum—15.5 g
Ketone—6.6 g
Pair-fed—6.2 g The weight of the daily food consumption of the rats in all three groups is presented in Table V. As is apparent from the data in the table, the food consumption of the rats on the diet containing 0.1% ketone was significantly less than that of the rats in the ad libidum group.

The change in mean body weights for the rats in the 3 groups throughout the period of the study is shown in Table VI. The mean value for the ad libidum group increased from 125.3 g at the initiation of the experiment to 166.3 g at the termination of the experiment. The mean value for the ketone group decreased from an initial value of 130.4 g to 117.3 g at the termination of the experiment. The mean value for the pair-fed group similarly decreased from an initial value of 128.0 g to a value of 113.6 at the termination of the experiment.

The mean percentage change in body weight from the initial values in the individual rats in the 3 groups is summarized in Table VII. The combined data indicates that the changes in body weight observed in the animals fed the ketone-containing diet were due to a suppression of food intake. The pair-fed animals (receiving only the amount of food consumed by the ketone-treated group) showed changes in body weight similar to that of the ketone-treated animals. That the marked decrease in the serum cholesterol concentrations in the rats treated with the ketone was not due to a reduction in food consumption is clearly shown by the fact that the serum cholesterol levels of the pair-fed group (whose food consumption and body weight values were essentially the same as the ketone-treated group) did not show a decrease during the period of study.

TABLE V

| FOOD CONSUMPTION (g) | | | |
|---|---|---|---|
| Day | Ad libidum | Ketone | Pair-fed |
| 0 | 12.2 ± 0.7 | 10.4 ± 0.7 | 14.2 ± 0.9 |
| 1 | 15.1 ± 0.6 | 5.1 ± 0.3 | 10.2 ± 0.6 |
| 2 | 15.1 ± 0.5 | 7.1 ± 0.3 | 5.0 ± 0.3 |
| 3 | 14.5 ± 0.7 | 5.5 ± 0.3 | 7.1 ± 0.3 |
| 4 | 13.7 ± 1.3 | 7.1 ± 0.5 | 5.4 ± 0.3 |
| 5 | 16.7 ± 0.7 | 5.8 ± 0.5 | 7.0 ± 0.5 |
| 6 | 16.8 ± 0.5 | 6.6 ± 0.5 | 5.8 ± 0.4 |
| 7 | 16.1 ± 0.4 | 7.5 ± 0.5 | 6.9 ± 0.5 |

TABLE VI

| BODY WEIGHT (g) | | | |
|---|---|---|---|
| Day | Ad libidum | Ketone | Pair-fed |
| 0 | 125.3 ± 4.4 | 130.4 ± 4.4 | 128.0 ± 4.0 |
| 1 | 123.2 ± 4.3 | 126.6 ± 4.8 | 128.9 ± 2.5 |
| 2 | 131.1 ± 4.5 | 121.4 ± 4.4 | 128.1 ± 2.2 |
| 3 | 138.2 ± 4.4 | 120.6 ± 4.6 | 122.9 ± 2.8 |
| 4 | 141.5 ± 3.2 | 118.5 ± 4.0 | 121.3 ± 2.3 |
| 5 | 147.0 ± 5.1 | 119.4 ± 4.3 | 117.7 ± 2.2 |
| 6 | 155.7 ± 4.7 | 118.9 ± 4.8 | 117.4 ± 2.5 |
| 7 | 162.0 ± 4.6 | 116.5 ± 4.9 | 114.6 ± 2.4 |
| 8 | 166.3 ± 4.6 | 117.3 ± 4.7 | 113.6 ± 3.2 |

TABLE VII

| PERCENTAGE CHANGE IN WEIGHT FROM INITIAL IN INDIVIDUAL RATS | | | |
|---|---|---|---|
| Day | Ad libidum | Ketone | Pair-fed |
| 1 | −1.7 ± 0.4 | −3.0 ± 0.7 | +1.1 ± 1.7 |
| 2 | +4.6 ± 0.6 | −7.0 ± 0.7 | +0.4 ± 1.8 |
| 3 | +10.3 ± 0.7 | −7.7 ± 0.7 | −3.8 ± 1.0 |
| 4 | +12.3 ± 1.9 | −9.1 ± 0.7 | −5.0 ± 1.4 |
| 5 | +17.4 ± 1.6 | −8.5 ± 0.5 | −7.7 ± 1.6 |
| 6 | +24.3 ± 0.9 | −8.7 ± 1.0 | −8.0 ± 1.7 |
| 7 | +30.1 ± 1.3 | −10.8 ± 1.3 | −10.2 ± 1.8 |
| 8 | +31.7 ± 1.9 | −10.2 ± 0.9 | −11.1 ± 1.7 |

EXAMPLE 44

Inhibition of Sterol Biosynthesis in L Cells and in Primary Cultures of Mouse Liver Cells The effect of various 15-oxygenated sterols on sterol biosynthesis in L cells and in primary cultures of mouse liver cells was tested essentially under conditions described in detail previously [A. A. Kandutsch and H. W. Chen, *J. Biol. Chem.*, Vol. 248, pp. 8408–8417 (1973) and A. A. Kandutsch and H. W. Chen, *J. Biol. Chem.*, Vol. 249, pp. 6057–6061 (1974')].

The primary liver cell cultures were prepared from 16-day-old (C57BL/6J fetuses and grown in chemically defined medium (serum-free) as described in the above cited publications. The L cells, a subline of NCTC clone 929 mouse fibroblasts, were grown in chemically defined medium (serum-free) as described in the publications. These L cells are transformed fibroblasts which are regarded as malignant since they will grow as tumors if injected into the mouse strain from which they were initially obtained.

The preparation of steroid-containing media, procedures for assays of the conversion of [1-$^{14}$C]acetate into digitonin-precipitable sterols, fatty acids, and $CO_2$ and methods for the measurement of DNA, protein, and HMG-CoA reductase were as described in the published articles. L cell cultures were preincubated with the 15-oxygenated sterols and their derivatives for 4 hours, then [1-$^{14}$C]acetate was added at a concentration of 4 μmoles per ml (4 μCi per ml); or the L cell cultures were incubated for 5 hours with the 15-oxygenated sterols before they were harvested for determination of microsomal HMG-CoA reductase activity.

Conditions for incubating the 15-oxygenated sterols or their derivatives with liver cell cultures were similar to those described for L cell cultures except that the cultures were incubated with the test compounds for 12 hours before labeled acetate was added or before they were harvested for enzyme assay.

The test compounds were tested over a range of at least 4 concentrations and the assay was repeated until the concentration of test compound required to produce 50% inhibition was located on the steeply declining portion of an activity vs. concentration plot. To diminish any possible effects of generalized differences in cellular metabolism, the rates of sterol synthesis from [1-$^{14}$C]acetate were calculated as the ratio of [$^{14}$C]sterols to [$^{14}$C]fatty acids as described in the two cited articles by Kandutsch and Chen.

In the experiments with the 15-oxygenated sterols presented below, none of the test compounds had any significant effect upon the rates at which the labeled acetate was incorporated into fatty acids or oxidized to carbon dioxide. This lack of an inhibitory effect upon the latter parameters of metabolism also indicates that the 15-oxygenated sterols and their derivatives were not generally toxic to the cells under the conditions studied.

Examples of the effects of a number of oxygenated derivatives of cholesterol (not including 15-oxygenated sterols) on sterol synthesis in these cell culture systems have been published in the two cited articles by Kandutsch and Chen. The sterol concentrations required to obtain 50% inhibition of sterol biosynthesis, as reported by Kandutsch and Chen, was as follows:

| | Concentrations (μM) Required for 50% Inhibition of Sterol Synthesis | |
|---|---|---|
| | L Cell Cultures | Primary Cultures of Liver Cells |
| Cholesterol | — | >5,200 |
| Cholest-5-en-3β-ol-22-one | 1.7 | 37.0 |
| Cholest-5-en-3β,22α-diol | 3.7 | 6.0 |
| Cholest-5-en-3β,25-diol | 0.07 | 1.0 |

It should be noted that pure cholesterol itself is inactive in the liver cell culture system. 25-Hydroxycholesterol had been the most potent inhibitor of sterol synthesis of this type prior to the present invention.

The results of studies of the action of a number of 15-oxygenated sterols on sterol synthesis in L cell and in primary cultures of liver cells are presented in Table VIII. As shown by the data in that table, a very large number of the compounds caused a 50% inhibition of sterol synthesis in the L cells at a concentration of $10^{-6}$ M or less. 14α-Ethyl-5α-cholest-7-en-3β, 15α diol caused a 50% inhibition of sterol synthesis in the L cells at a concentration of $5 \times 10^{-8}$ M. 14α-ethyl-5α-cholest-7-en-15α-ol-3-one and 14α-ethyl-5α-cholest-7-en-3α-ol-15-one are extraordinary active, giving essentially 100% inhibition of sterol synthesis at a concentration at $10^{-7}$ M.

Since liver is a major site of the biosynthesis of cholesterol in animal cells, the finding that a significant number of the compounds are inhibitory to the sterol synthesis in the liver cells is especially important. It should be noted that 14α-ethyl-5α-cholest-7-en-3β,15α-diol is extraordinarily active in this respect and causes a 50% inhibition of sterol synthesis at a concentration of $6 \times 10^{-8}$ M which is considerably lower than the previously reported lowest value of $10^{-6}$ M for 25-hydroxycholesterol.

TABLE VIII

| | Concentrations (μM) Required for 50% Inhibition of Sterol Synthesis | |
|---|---|---|
| | L Cell Cultures | Primary Cultures of Liver cells |
| 5α-Cholest-8(14)-en-3β-ol-15-one | 0.1 | 4.0 |
| 5α-Cholest-8(14)-en-3β,15β-diol | 1.8 | 10.3 |
| 5α-Cholest-8(14)-en-3β,15α-diol | 3.7 | 31.0 |
| 5α-Cholest-8(14)-en-3β,7ξ,15ξ-triol | 5.0 | 4.8 |
| 5α-Cholest-8(14)-en-3α-ol-15-one | 0.5 | — |
| 3β-Hemisuccinoyloxy-5α-cholest-8(14)-en-15-one | 3.2 | — |
| 3β-Hexadecanoyloxy-5α-cholest-8(14)-en-15-one | >16 | — |
| 5α,14β-Cholest-7-en-3β,15β-diol | 1.0 | 2.5 |
| 5α,14β-Cholest-7-en-3β,15α-diol | 3.2 | 7.5 |
| 5α,14β-Cholest-7-en-15β-ol-3-one | 0.25 | — |
| 5α,14β-Cholest-7-en-15α-ol-3-one | 2.0 | — |
| 14α-Methyl-5α-cholest-7-en-3β-ol-15-one | 0.3 | 4.5 |
| 14α-Methyl-5α-cholest-7-en-3β,15β-diol | 0.5 | — |
| 14α-Methyl-5α-cholest-7-en-3β,15α-diol | 0.3 | 1.8 |
| 3β-Methoxy-14α-methyl-5α-cholest-7-en-15-one | 20.0 | — |
| 3β-Methoxy-14α-methyl-5α-cholest-7-en-15β-ol | 1.4 | 3.5 |
| 3β-Methoxy-14α-methyl-5α-cholest-7-en-15α-ol | 0.3 | 1.9 |
| 14α-Ethyl-5α-cholest-7-en-3β,15β-diol | 0.4 | 0.8 |
| 14α-Ethyl-5α-cholest-7-en-3β,15α-diol | 0.5 | 0.06 |
| 14α-Ethyl-5α-cholest-7-en-3β-ol-15-one | 0.3 | 2.1 |
| 3β-Ethoxy-14α-ethyl-5α-cholest-7-en-15-ol | 0.7 | 4.3 |
| 3β-Ethoxy-14α-ethyl-5α-cholest-7-en-15-one | >22.0 | — |
| 14α-Ethyl-5α-cholest-7-en-15α-ol-3-one | <0.1* | — |
| 14α-Ethyl-5α-cholest-7-en-3α-ol-15-one | <0.1* | — |
| 3β-Hexadecanoyloxy-14α-ethyl-5α-cholest-7-en-15α-ol | 7.0 | — |
| 3β-Hexadecanoyloxy-14α-ethyl-5α-cholest-7-en-15β-ol | >15.10 | — |
| 3β-Acetoxy-14α-ethyl-5α-cholest-7-en-15β-ol | 0.03 | — |
| 14α-n-Propyl-5α-cholest-7-en-3β,15β-diol | 4.1 | — |
| 14α-n-Propyl-5α-cholest-7-en-3β,15α-diol | 1.1 | — |

TABLE VIII-continued

| | Concentrations (μM) Required for 50% Inhibition of Sterol Synthesis | |
|---|---|---|
| | L Cell Cultures | Primary Cultures of Liver cells |
| 14α-n-Propyl-5α-cholest-7-en-3β-ol-15-one | 3.4 | — |
| 14α-n-Butyl-5α-cholest-7-en-3β,15α-diol | 5.0 | — |
| 14α-n-Butyl-5α-cholest-7-en-3β,15β-diol | 4.4 | — |
| 14α-n-Butyl-5α-cholest-7-en-3β-ol-15-one | 8.3 | — |

*Essentially 100% inhibition was observed at this concentration.

EXAMPLE 45

Reduction in HMG-CoA Reductase in Cells by 15-Oxygenated Sterols

A number of the 15-oxygenated sterols have also been tested with respect to their effects on the activity and/or levels of the enzyme HMG-CoA reductase (3-hydroxy-3-methylglutaryl coenzyme A reductase) in the L cells and in the liver cells. As noted previously, this enzyme catalyzes the reduction of 3-hydroxy-3-methylglutaryl coenzyme A to yield mevalonic acid, an essential intermediate in the biosynthesis of sterols and of a number of other essential compounds in cells.

Using the technique described by Kandutsch and Chen in the article cited in the previous example, the concentrations of various 15-oxygenated sterols required to reduce the levels of activity of HMG-CoA reductase by 50% was determined in the cells of the L cells in culture and of the primary cultures of liver cells. The data obtained from these tests are reported in Table IX.

TABLE IX

| | Concentrations (μM) Required for 50% Reduction of the Activity of HMG-CoA Reductase in: | |
|---|---|---|
| | L Cell Cultures | Primary Cultures of Liver Cells |
| 5α-Cholest-8(14)-en-3β-ol-15-one | 0.3 | 4.0 |
| 5α-Cholest-8(14)-en-3β,15β-diol | 2.5 | 16.1 |
| 5α-Cholest-8(14)-en-3β,7ξ,15ξ-triol | 1.9 | 18.0 |
| 5α,14β-Cholest-7-en-3β,15β-diol | 4.5 | 6.0 |
| 5α,14β-Cholest-7-en-3β,15α-diol | 6.7 | 12.5 |
| 14α-Methyl-5α-cholest-7-en-3β-ol-15-one | 0.3 | 2.8 |
| 14α-Methyl-5α-cholest-7-en-3β,15β-diol | 1.2 | 4.3 |
| 14α-Methyl-5α-cholest-7-en-3β,15α-diol | 0.3 | 2.0 |
| 3β-Methoxy-14α-methyl-5α-cholest-7-en-15β-ol | 3.7 | 3.5 |
| 3β-Methoxy-14α-methyl-5α-cholest-7-en-15α-ol | 3.0 | 1.6 |
| 3β-Acetoxy-14α-ethyl-5α-cholest-7-en-15β-ol | 0.13 | — |
| 14α-Ethyl-5α-cholest-7-en-3β-ol-15-one | 1.9 | 2.1 |
| 3β-Hemisuccinoyloxy-5α-cholest-8(14)-en-15-one | 3.0 | — |

It can be seen by a comparison of the data in Table IX with the data in Table VIII that with many, but not all, of the compounds, the concentrations required to cause a 50% reduction in the level of the enzyme activity for HMG-CoA reductase in the cells were very similar to the concentrations required of the same compounds to cause a 50% inhibition of sterol biosynthesis.

EXAMPLE 46

Another experiment following essentially the procedure of Example 43 was performed in which the 5α-cholest-8(14)-en-3β-ol-15-one was incorporated into the Cholesterol Free Test Diet at a concentration of 0.2%.

At the initiation of the experimental period the mean body weight values (g) (± standard error of mean) for the 3 groups were as follows:
Ad libidum—141.2±6.6
Ketone—152.3±5.5
Pair-fed—153.2±6.4

At the initiation of the experimental period the mean serum cholesterol concentrations (mg per 100 ml of serum ± standard error of mean) for the 3 groups were as follows:
Ad libidum—7.43±3.9
Ketone—80.5±2.8
Pair-fed—91.4±3.6

As is apparent, the groups in this particular experiment were not especially well-matched, especially with respect to the initial mean serum cholesterol concentrations. Despite this fact, the 5α-cholest-8(14)-en-15-on-3α-ol administered in the diet had a marked effect on the serum cholesterol concentration.

The results of this experiment are presented in Table X. As shown in the table, the mean serum cholesterol level (mg per 100 ml of serum) of the rats receiving the 0.2% 5α-cholest-8(14)-en-3β-ol-15-one in the diet decreased from an intitial value of 80.5 to a value of 73.2 on day 4, 32.2 on day 7, and 30.3 on day 9. The mean serum cholesterol level of the ad libidum group rose very slightly on day 3 but was essentially unchanged throughout the period of the experiment. However, in this particular experiment the mean serum cholesterol concentration in the pair-fed group did not remain unchanged throughout the experiment. The serum cholesterol concentration dropped from an initial value of 91.4 to 62.9 on day 7 and to 55.1 on day 9, presumably as a result of the marked food restriction in this experiment.

TABLE X

| SERUM CHOLESTEROL CONCENTRATION (mg per 100 ml) | | | |
|---|---|---|---|
| Day | Ad libidum | Ketone | Pair-fed |
| 0 | 74.3 ± 3.9 | 80.5 ± 2.8 | 91.4 ± 3.6 |
| 4 | 80.1 ± 3.9 | 73.2 ± 3.0 | 91.8 ± 6.0 |
| 7 | 81.2 ± 3.2 | 32.2 ± 5.9 | 62.9 ± 4.5 |
| 9 | 81.8 ± 1.6 | 30.3 ± 6.2 | 55.1 ± 6.5 |

The data on the serum cholesterol levels for the 3 groups as a percentage of the value of the initial level (Day 0) in the individual rats after 4, 7, and 9 days are presented in Table XI.

TABLE XI
SERUM CHOLESTEROL LEVELS - PERCENTAGE OF INITIAL LEVELS IN INDIVIDUAL RATS

| Day | Ad libidum | Ketone | Pair-fed |
| --- | --- | --- | --- |
| 4 | 109.9 ± 6.1 | 91.6 ± 4.3 | 101.0 ± 4.1 |
| 7 | 111.1 ± 7.4 | 40.6 ± 7.9 | 70.2 ± 5.3 |
| 9 | 111.9 ± 6.0 | 37.9 ± 8.8 | 60.9 ± 8.0 |

The changes in mean body weights for the rats in the 3 groups throughout the study are shown in Table XII. The mean value for the ad libidum group increased from 141.2 g at the initiation of the experiment to 178.2 g at the termination of the experiment. The mean value for the ketone group decreased from an initial level of 152.3 g to 122.3 g at the termination of the experiment. The mean value for the pair-fed group similarly decreased from an initial value of 153.2 g to a value of 114.4 g at the termination of the experiment.

TABLE XII
BODY WEIGHT (g)

| Day | Ad libidum | Ketone | Pair-fed |
| --- | --- | --- | --- |
| 0 | 141.2 ± 6.6 | 152.3 ± 5.5 | 153.2 ± 6.4 |
| 1 | 143.5 ± 7.1 | 151.3 ± 4.7 | 157.2 ± 8.0 |
| 2 | 149.7 ± 7.3 | 145.4 ± 4.9 | 152.9 ± 7.6 |
| 3 | 153.0 ± 7.9 | 139.0 ± 4.8 | 145.1 ± 7.4 |
| 4 | 161.4 ± 6.5 | 137.4 ± 4.9 | 139.0 ± 7.0 |
| 5 | 165.4 ± 6.6 | 134.5 ± 4.5 | 133.1 ± 6.7 |
| 6 | 170.4 ± 6.6 | 130.7 ± 5.1 | 127.6 ± 3.9 |
| 7 | 177.3 ± 7.1 | 127.7 ± 5.2 | 120.1 ± 3.9 |
| 8 | 178.2 ± 7.8 | 122.3 ± 5.8 | 114.4 ± 4.0 |

As shown by the data in Table XIII, the food consumption of the rats on the 0.2% ketone diet was significantly less than that of the rats in the ad libidum group.

TABLE XIII
DAILY FOOD CONSUMPTION (g)

| Day | Ad libidum | Ketone | Pair-fed |
| --- | --- | --- | --- |
| 0 | 12.4 ± 1.3 | 7.2 ± 0.6 | 13.6 ± 1.4 |
| 1 | 13.2 ± 1.4 | 4.4 ± 1.1 | 3.8 ± 0.9 |
| 2 | 14.0 ± 1.6 | 4.8 ± 0.4 | 4.3 ± 0.4 |
| 3 | 16.5 ± 0.4 | 4.8 ± 0.2 | 4.5 ± 0.4 |
| 4 | 15.1 ± 0.8 | 5.5 ± 0.4 | 4.5 ± 0.4 |
| 5 | 16.7 ± 0.5 | 5.5 ± 0.3 | 5.3 ± 0.4 |
| 6 | 17.8 ± 0.3 | 5.4 ± 0.2 | 5.4 ± 0.3 |
| 7 | 14.5 ± 1.1 | 5.1 ± 0.2 | 5.1 ± 0.2 |
| 8 | 15.9 ± 0.7 | 4.3 ± 0.6 | 4.9 ± 0.3 |

On day 8 of the experiment it was noted that 4 of the rats in the ketone group were developing diarrhea. One of these rats died the following day. Two other rats in this group showed loose stools on day 9.

EXAMPLE 47

Another dietary experiment with 5β-cholest-8(14)-en-3β-ol-15-one was performed using 7-week-old mice. Five mice were fed the ketone at a level of 0.2% in a diet which was essentially free of animal sterols for eight days. Five control pair-fed mice were fed the same diet to which the ketone was not added. The mean plasma cholesterol concentration in the ketone group after the eight day experiment was 35.8(±3.6, standard error of mean) mg per 100 ml of plasma while the corresponding value for the pair-fed group was 114.4 (±3.4, standard error of mean). It should be noted that very closely matched pairfeeding is difficult to perform in mice of this age due to the small amounts of food which are consumed and which must be accurately determined in such experiments. The ketone group showed an average decrease in body weight over the period of the study of 5.9 g (±0.1, standard error of mean). The control pair-fed group showed an average decrease in body weight of 2.4 g (±0.1, standard error of mean).

Two other oxygenated sterols, 25-hydroxycholesterol and 7-ketocholesterol, which have been shown to have strong inhibitory action on the synthesis of sterols in L cells in culture and in the primary cultures of mouse liver cells, have been found to have no significant plasma cholesterol-lowering effect in mice (A.A. Kandutsch, H.-J. Heiniger, and H. W. Chen, Biochimica et Biophysica Acta, 486, 260–272, 1977). Although the present invention has been described in connection with preferred embodiments, it is understood that modifications and variations may be resorted to without departing from the spirit and scope of the invention. Such modifications are considered to be within the purview and scope of the invention and the appended claims.

We claim:

1. A method of inhibiting the biosynthesis of mevalonic acid, and the effects derived therefrom, which comprises administering to a host an amount effective to inhibit biosynthesis of mevalonic acid of a sterol biosynthesis inhibiting 15-oxgenated sterol, said 15-oxygenated sterol having the structural formula:

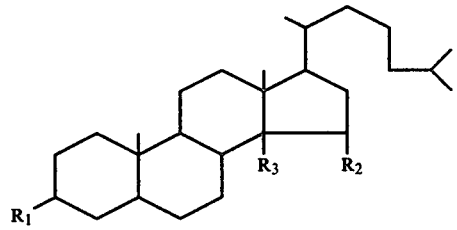

where:
$R_1$ is —OH, =O, —OR$_4$,

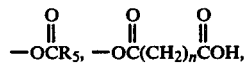

a sulfate group, or
a Mg, Na, or K salt of a sulfate group;
$R_2$ is —OH, =O, or

$R_3$ is non-existent when there is a double bond between the 8 and 14 carbon atoms or αH, βH, or an αC$_1$ to C$_6$ alkyl group;
$R_4$ is a C$_1$ to C$_6$ alkyl group;
$R_5$ is a C$_1$ to C$_{20}$ aliphatic group, or a phenyl group, provided that when R$_5$ forms part of the R$_2$ substituent, R$_5$ is a C$_1$ to C$_{20}$ aliphatic group; and
n is a whole number from 2 to 6, with said R$_1$ and R$_2$ substituents, other than when they are =O, being in either the α or β position.

2. The method of claim 1 wherein said 15-oxygenated sterol is 5α-cholest-8 (14)-en-3β-ol-15-one.

3. The method of claim 1 wherein said 15-oxygenated sterol is 5α-cholest-8(14)-en-3β, 15β-diol.

4. The method of claim 1 wherein said 15-oxygenated sterol is 5α-cholest-8(14)-en-3β, 15α-diol.

5. The method of claim 1 wherein said 15-oxygenated sterol is 5α, 14β-cholest-7-en-3β, 15α-diol.

6. The method of claim 1 wherein said 15-oxygenated sterol is 5α, 14β-cholest-7-en-3β, 15β-diol.

7. The method of claim 1 wherein said 15-oxygenated sterol is 14α-methyl-5α-cholest-7-en-3β-ol-15-one.

8. The method of claim 1 wherein said 15-oxygenated sterol is 14α-methyl-5α-cholest-7-en-3β, 15β-diol.

9. The method of claim 1 wherein said 15-oxygenated sterol is 14α-methyl-5α-cholest-7-en-3β, 15α-diol.

10. The method of claim 1 wherein said 15-oxygenated sterol is 3β-methoxy-14α-methyl-5α-cholest-7-en-15 one.

11. The method of claim 1 wherein said 15 oxygenated sterol is 3β-ethoxy-14α-ethyl-5α-cholest-7-en-15α-ol.

12. The method of claim 1 wherein said 15 oxygenated sterol is 3β-methoxy-14α-methyl-5α-cholest-7-en-15α-ol.

13. The method of claim 1 wherein said 15 oxygenated sterol is 14α-ethyl-5α-cholest-7-en-3β-ol-15-one.

14. The method of claim 1 wherein said 15 oxygenated sterol is 14α-ethyl-5α-cholest-7-en-3β,15α-diol.

15. The method of claim 1 wherein said 15-oxygenated sterol is administered in a dosage equivalent to from about 0.1 mg to about 140 mg of said 15-oxygenated sterol per day per kg. weight of said host.

16. A pharmaceutical composition which comprises a pharmaceutically acceptable carrier in combination with an amount which is non-toxic but effective to inhibit biosynthesis of mevalonic acid of a mevalonic acid biosynthesis inhibiting 15-oxygenated sterol, said 15-oxygenated sterol having the structural formula:

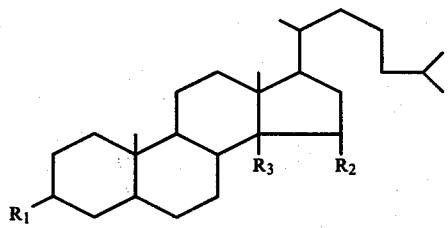

$R_1$ is —OH, =O, —OR$_4$

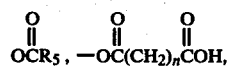

a sulfate group, or a
Mg, Na, or K salt of a sulfate group;
$R_2$ is —OH, =O, or

$R_3$ is non-existent when there is a double bond between the 8 and 14 carbon atoms, or αH, βH, or an αC$_1$ to C$_6$ alkyl group;
$R_4$ is a C$_1$ to C$_6$ alkyl group;

$R_5$ is a C$_1$ to C$_{20}$ aliphatic group, or a phenyl group, provided that when R$_5$ forms part of the R$_2$ substituent, R$_5$ is a C$_1$ to C$_{20}$ aliphatic group; and n is a whole number from 2 to 6, with said R$_1$ and R$_2$ substituents, other than when they are =O, being in either the α or β position.

17. The composition of claim 16 wherein the 15-oxygenated sterol is present in an amount of about 0.1 mg to about 140 mg.

18. A method of inhibiting the biosynthesis of sterols, including all effects derived therefrom, which comprises administering to a host the pharmaceutical composition of claim 16 in a dosage equivalent to about 0.1 mg. to about 140 mg. of said 15-oxygenated sterol per day per kg. weight of said host.

19. The pharmaceutical composition of claim 16 wherein said 15-oxygenated sterol is 5α-cholest-8(b 14)-en-3β-ol-15-one.

20. The pharmaceutical composition of claim 16 wherein said 15-oxygenated sterol is 5α-cholest-8(14)-en-3β, 15β-diol.

21. The pharmaceutical composition of claim 16 wherein said 15-oxygenated sterol is 5α-cholest-8(14)-en-3β, 15α-diol.

22. The pharmaceutical composition of claim 16 wherein said 15-oxygenated sterol is 5α, 14β-cholest-7-en-3β, 15α-diol.

23. The pharmaceutical composition of claim 16 wherein said 15-oxygenated sterol is 5α, 14β-cholest-7-en-3β, 15β-diol.

24. The pharmaceutical composition of claim 16 wherein said 15-oxygenated sterol is 14α-methyl-5α-cholest-7-en-3β-ol-15-one.

25. The pharmaceutical composition of claim 16 wherein said 15-oxygenated sterol is 14α-methyl-5α-cholest-7-en-3β,15β-diol.

26. The pharmaceutical composition of claim 16 wherein said 15-oxygenated sterol is 14α-methyl-5α-cholest-7-en-3β,15α-diol.

27. The pharmaceutical composition of claim 16 wherein said 15-oxygenated sterol is 3β-methoxy-14α-methyl-5αcholest-7-en-15-one.

28. The pharmaceutical compositon of claim 16 wherein said 15-oxygenated sterol is 3β-methoxy-14α-ethyl-5α-cholest-7-en-15α-ol.

29. The pharmaceutical compositon of claim 16 wherein said 15-oxygenated sterol is 3β-methoxy-14α-methyl-5α-cholest-7-en-15α-ol.

30. The pharmaceutical compositon of claim 16 wherein said 15-oxygenated sterol is 14α-ethyl-5α-cholest-7-en-3α-ol-15-one.

31. The pharmaceutical composition of claim 16 wherein said 15-oxygenated sterol is 14α-ethyl-5α-cholest-7-en-3α, 15α-diol.

32. A method of suppressing appetite which comprises administering to a subject an amount effect to suppress appetite of an appetite suppressing 15-oxygenated sterol having the structural formula:

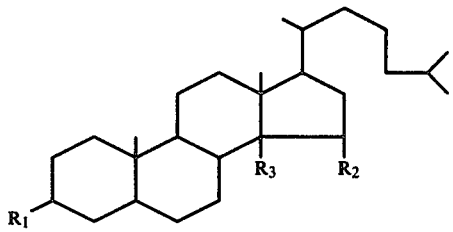

where:
R$_1$ is —OH, =O, —OR$_4$,

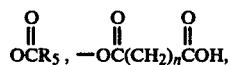

a sulfate group, or a Mg, Na, or K salt of a sulfate group;
R$_2$ is —OH, =O, or

R$_3$ is non-existent when there is a double bond between the 8 and 14 carbon atoms or αH, βH, or an αC$_1$ to C$_6$ alkyl group;
R$_4$ is a C$_1$ to C$_6$ alkyl group;
R$_5$ is a C$_1$ to C$_{20}$ aliphatic group, or a phenyl group, provided that when R$_5$ forms part of the R$_2$ substituent, R$_5$ is a C$_1$ to C$_{20}$ aliphatic group; and
n is a whole number from 2 to 6, with said R$_1$ and R$_2$ substituents, other than when they are =O, being in either the α or β position.

33. The method of claim 32 wherein said 15-oxygenated sterol is administered in a dosage equivalent to from about 0.1 mg to about 140 mg of said 15-oxygenated sterol per day per kg weight of said subject.

34. A method of suppressing appetite comprising administering to a subject the pharmaceutical composition of claim 16 is a dosage equivalent to about 0.1 mg to about 140 mg of said 15-oxygenated sterol per day per kg weight of said host.

35. A method of suppressing cell growth comprising administering to a host an amount effective to suppress cell growth of a cell growth suppressing 15-oxygenated sterol having the structural formula:

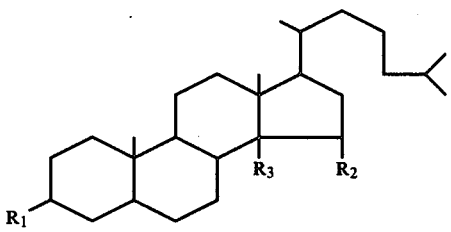

where:
R$_1$ is —OH, =O, —OR$_4$,

a sulfate group, or a Mg, Na, or K salt of a sulfate group;
R$_2$ is —OH, =O, or

R$_3$ is non-existent when there is a double bond between the 8 and 14 carbon atoms or αH, βH, or an αC$_1$ to C$_6$ alkyl group;
R$_4$ is a C$_1$ to C$_6$ alkyl group;
R$_5$ is a C$_1$ to C$_{20}$ aliphatic group, or a phenyl group, provided that when R$_5$ forms part of the R$_2$ substituent, R$_5$ is a C$_1$ to C$_{20}$ aliphatic group; and
n is a whole number from 2 to 6, with said R$_1$ and R$_2$ substituents, other than when they are =O, being in the α or β position.

36. A method of inhibiting cell growth comprising administering to host the pharmaceutical composition of claim 16 in a dosage equivalent to about 0.1 mg. to about 140 mg. of said 15-oxygenated sterol per day per kg. weight of said host.

37. A method of suppressing the formation of cholesterol in the serum of a subject comprising administering to a subject the pharmaceutical composition of claim 16 in a dosage equivalent to about 0.1 gm. to about 140 mg. of said 15-oxygenated sterol per day per kg. weight of said host.

38. The method of claim 1 wherein said oxygenated sterol has a double bond between the 8 and 14 carbon atoms and there is no R$_3$ substituent.

39. The method of claim 1 wherein said oxygenated sterol has a double bond between the 7 and 8 carbon atoms.

40. A method of suppressing the serum cholesterol level in a host comprising administering to said host an amount effective to suppress serum cholesterol of a sterol biosynthesis inhibiting 15-oxygenated sterol, said 15-oxygenated sterol having the structural formula:

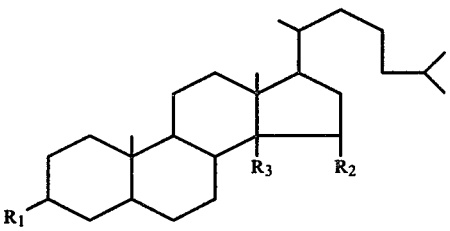

R$_1$ is —OH, =O, —OR$_4$,

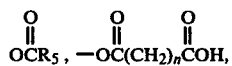

a sulfate group, or a Mg, Na, or K salt of a sulfate group;
R$_2$ is —OH, =O, or

R$_3$ is non-existent when there is a double bond between the 8 and 14 carbon atoms or αH, 62 H, or an αC$_1$ to C$_6$ alkyl group;

$R_4$ is a $C_1$ to $C_6$ alkyl group;

$R_5$ is a $C_1$ to $C_{20}$ aliphatic group, or a phenyl group, provided that when $R_5$ forms part of the $R_2$ substituent, $R_5$ is a $C_1$ to $C_{20}$ aliphatic group; and n is a whole number from 2 to 6, with said $R_1$ and $R_2$ substituents, other than when they are =O, being either the $\alpha$ or $\beta$ position.

41. The method of claim 40 wherein said 15-oxygenated sterol is 5$\alpha$-cholest-8(14)-en-3$\beta$-ol-15-one.

42. The method of claim 40 wherein said 15-oxygenated sterol is 5$\alpha$-cholest-8(14)-en-3$\alpha$, 15$\beta$-diol.

43. The method of claim 40 wherein said 15-oxygenated sterol is 5$\alpha$-cholest-8(14)-en-3$\alpha$, 15$\alpha$-diol.

44. The method of claim 40 wherein said 15-oxygenated sterol is 5$\alpha$, 14$\beta$-cholest-7-en-3$\beta$, 15$\alpha$-diol.

45. The method of claim 40 wherein said 15-oxygenated sterol is 5$\alpha$, 14$\beta$-cholest-7-en-3$\beta$, 15$\beta$-diol.

46. The method of claim 40 wherein said 15-oxygenated sterol is 14$\alpha$-methyl-5$\alpha$-cholest-7-en-3$\beta$-ol-15-one.

47. The method of claim 40 wherein said 15-oxygenated sterol is 14$\alpha$-methyl-5$\alpha$-cholest-7-en-3$\beta$, 15$\beta$-diol.

48. The method of claim 40 wherein said 15-oxygenated sterol is 14$\alpha$-methyl-5$\alpha$-cholest-7-en-3$\beta$, 15$\alpha$-diol.

49. The method of claim 40 wheren said 15-oxygenated sterol is 3$\beta$-methoxy-14$\alpha$-methyl-5$\alpha$-cholest-7-en-15-one.

50. The method of claim 40 wherein said 15-oxygenated sterol is 3$\beta$-ethyl-14$\alpha$-ethyl-5$\alpha$-cholest-7-en-15$\alpha$-ol.

51. The method of claim 40 wherein said 15-oxygenated sterol is 3$\beta$-methoxy-14$\alpha$-methyl-5$\alpha$-cholest-7-en-15$\alpha$-ol.

52. The method of claim 40 wherein said 15-oxygenated sterol is 14$\alpha$-ethyl-5$\alpha$-cholest-7-en-3$\beta$-ol-15-one.

53. The method of claim 40 wherein said 15-oxygenated sterol is 14$\alpha$-ethyl-5$\alpha$-cholest-7-en-3$\beta$, 15$\alpha$-diol.

54. The method of claim 40 wherein said 15-oxygenated sterol is 14$\alpha$-ethyl-5$\alpha$-cholest-7-en-15$\alpha$-ol-3-one.

55. The method of claim 40 wherein said 15-oxygenated sterol is administered in a dosage equivalent to from about 0.1 mg. to about 140 mg of said 15-oxygenated sterol per day per kg. weight of said host.

56. The method of claim 40 wherein said oxygenated sterol has a double bond between the 8 and 14 carbon atoms and there is no $R_3$ substituent.

57. The method of claim 40 wherein said oxygenated sterol has a double bond between the 7 and 8 carbon atoms.

58. The method of claim 16 wherein said oxygenated sterol has a double bond between the 8 and 14 carbon atoms and there is no $R_3$ substituent.

59. The method of claim 16 wherein said oxygenated sterol has a double bond between the 7 and 8 carbon atoms.

60. The method of claim 32 wherein said oxygenated sterol has a double bond between the 8 and 14 carbon atoms and there is no $R_3$ substituent.

61. The method of claim 32 wherein said oxygenated sterol has a double bond between the 7 and 8 carbon atoms.

62. The method of claim 35 wherein said oxygenated sterol has a double bond between the 8 and 14 carbon atoms and there is no $R_3$ substituent.

63. The method of claim 35 wherein said oxygenated sterol has a double bond between the 7 and 8 carbon atoms.

* * * * *

UNITED STATES PATENT AND TRADEMARK OFFICE
CERTIFICATE OF CORRECTION

PATENT NO. : 4,202,891
DATED : May 13, 1980
INVENTOR(S) : George J. Schroepfer, Jr., Edward J. Parish It is certified that error appears in the above-identified patent and that said Letters Patent are hereby corrected as shown below:

Claim 16, column 49, line 50, insert --where:--;

Claim 19, column 50, line 20, should read --$5\alpha$-cholest-8(14)--;

Claim 27, column 50, line 50, should read --$5\alpha$-cholest--;

Claim 34, column 51, line 43, change "is" to --in--;

Claim 40, column 52, line 53, insert --where:--;

line 67, "62H" should be --$\beta$ H--;

column 53, line 7, before "either" insert --in--;

Claim 42, column 53, line 11, change "$3\alpha$" to --$3\beta$--;

Claim 43, column 53, line 13, change "$3\alpha$" to --$3\beta$--.

Signed and Sealed this

Fourth Day of November 1980

[SEAL]

Attest:

SIDNEY A. DIAMOND

Attesting Officer

Commissioner of Patents and Trademarks